United States Patent [19]
Leone-Bay et al.

[11] Patent Number: 6,071,510
[45] Date of Patent: Jun. 6, 2000

[54] MODIFIED AMINO ACIDS AND COMPOSITIONS COMPRISING THE SAME FOR DELIVERING ACTIVE AGENTS

[75] Inventors: Andrea Leone-Bay, Ridgefield, Conn.; Koc-Kan Ho, Mt. Kisco, N.Y.; Jeffery Bruce Press, Brewster, N.Y.; Nai-Fang Wang, Long Island, N.Y.

[73] Assignee: Emisphere Technologies, Inc., Tarrytown, N.Y.

[21] Appl. No.: 08/839,094

[22] Filed: Apr. 23, 1997

Related U.S. Application Data

[63] Continuation of application No. 08/414,654, Mar. 31, 1995, Pat. No. 5,650,386.

[51] Int. Cl.[7] .......................... A61K 31/70; A61K 38/17; A61K 47/12; C07C 229/06
[52] U.S. Cl. .................. 424/85.2; 424/85.4; 424/141.1; 424/184.1; 514/2; 514/3; 514/11; 514/12; 514/21; 514/56; 514/773; 514/784; 546/323; 548/537; 549/72; 554/94; 554/106; 554/111; 554/112; 562/430; 562/444; 562/449; 562/450; 562/507; 562/567
[58] Field of Search ................. 424/85.2, 85.4, 424/141.1, 184.1; 514/2, 3, 11, 12, 21, 56, 773, 784, 562, 354, 448, 423, 563; 562/444, 449, 450, 507, 567, 430; 546/323; 549/72; 548/537; 554/94, 106, 111, 112

[56] References Cited

U.S. PATENT DOCUMENTS

| | | | |
|---|---|---|---|
| Re. 24,899 | 11/1960 | Green | 428/402.2 |
| 2,671,451 | 3/1954 | Bolger | 128/260 |
| 2,828,206 | 3/1958 | Rosenberg | 99/2 |
| 2,862,918 | 12/1958 | Meyer et al. | 260/123.5 |
| 2,868,740 | 1/1959 | Luce | 260/8 |
| 2,971,916 | 2/1961 | Schleicher et al. | 252/62.5 |
| 3,016,308 | 1/1962 | Macaulay | 177/37 |
| 3,052,655 | 9/1962 | Fox et al. | 260/78 |
| 3,057,344 | 10/1962 | Abella et al. | 128/2 |
| 3,076,790 | 2/1963 | Fox et al. | 260/78 |
| 3,170,802 | 2/1965 | Fukushima | 99/145 |
| 3,190,837 | 6/1965 | Brynko et al. | 252/316 |
| 3,474,777 | 10/1969 | Figge et al. | 128/2 |
| 3,491,093 | 1/1970 | Pachter et al. | 260/247.5 |
| 3,565,559 | 2/1971 | Sato | 424/37 |
| 3,567,650 | 3/1971 | Bakan | 252/316 |
| 3,574,832 | 4/1971 | Engel et al. | 424/183 |
| 3,576,758 | 4/1971 | Emrick | 252/316 |
| 3,687,926 | 8/1972 | Arima et al. | 260/112.5 |
| 3,725,113 | 4/1973 | Chang | 117/82 |
| 3,748,277 | 7/1973 | Wagner | 252/316 |
| 3,794,561 | 2/1974 | Matsukawa et al. | 195/29 R |
| 3,795,739 | 3/1974 | Birkmayer et al. | 424/274 |
| 3,816,404 | 6/1974 | Kablaoui et al. | 260/239.3 |
| 3,822,348 | 7/1974 | Higashi et al. | 424/95 |
| 3,849,550 | 11/1974 | Teitelbaum | 424/78 |
| 3,933,873 | 1/1976 | Love et al. | 260/239.3 |
| 3,937,668 | 2/1976 | Zolle | 252/316 |
| 3,939,253 | 2/1976 | Bodor et al. | 424/309 |
| 3,956,172 | 5/1976 | Saeki et al. | 252/316 |
| 3,962,416 | 6/1976 | Katzen | 424/19 |
| 3,976,773 | 8/1976 | Curran | 424/250 |
| 4,035,507 | 7/1977 | Bodor et al. | 424/311 |
| 4,048,268 | 9/1977 | Ludwig | 264/15 |
| 4,061,466 | 12/1977 | Sjoholm et al. | 23/230 B |
| 4,117,801 | 10/1978 | Dannelly et al. | 118/20 |
| 4,147,767 | 4/1979 | Yapel | 424/22 |
| 4,183,849 | 1/1980 | Hansen | 260/112.7 |
| 4,199,561 | 4/1980 | Roth et al. | 424/32 |
| 4,217,370 | 8/1980 | Rawlings et al. | 426/98 |
| 4,238,506 | 12/1980 | Stach et al. | 424/319 |
| 4,239,635 | 12/1980 | Rieder | 252/34 |
| 4,239,754 | 12/1980 | Sache et al. | 424/183 |
| 4,272,506 | 6/1981 | Schwarzberg | 424/8 |
| 4,289,759 | 9/1981 | Heavner et al. | 424/177 |
| 4,345,588 | 8/1982 | Widder et al. | 128/1.3 |

(List continued on next page.)

FOREIGN PATENT DOCUMENTS

| | | | |
|---|---|---|---|
| 1077842 | 8/1976 | Canada | A61K 9/50 |
| 0 000 667 A1 | 2/1979 | European Pat. Off. | A61K 9/50 |
| 0 036 145 A1 | 9/1981 | European Pat. Off. | A61K 31/62 |
| 0 068 314 | 1/1983 | European Pat. Off. | A61K 31/16 |
| 0 105 804 | 4/1984 | European Pat. Off. | C12N 15/00 |
| 0 130 162 A2 | 1/1985 | European Pat. Off. | B01J 13/02 |
| 0 170 540 A1 | 2/1986 | European Pat. Off. | A61K 9/52 |
| 226223-A2 | 6/1987 | European Pat. Off. | C07C 103/46 |
| 0 342 054 A2 | 11/1989 | European Pat. Off. | A61K 7/06 |
| 0 342 056 A2 | 11/1989 | European Pat. Off. | A61K 7/06 |
| 0 365 183 | 4/1990 | European Pat. Off. | A61K 31/18 |
| 0 366 277 | 5/1990 | European Pat. Off. | A61K 9/107 |
| 0 418 642 | 3/1991 | European Pat. Off. | A61K 37/30 |
| 0 448 057 | 9/1991 | European Pat. Off. | C12P 21/08 |
| 0 452 161 | 10/1991 | European Pat. Off. | A61K 7/48 |
| 0 459 795 | 12/1991 | European Pat. Off. | A61K 37/02 |

(List continued on next page.)

OTHER PUBLICATIONS

Airaudo, C.B. et al. (1987) *Journal of Food Science,* vol. 52(6), pp. 1750–1752.
Andini, S. et al. (1975) *Origins of Life,* vol. 6, pp. 147–153.
Brooke, S. 1 et al. (1977) *BioSystems,* vol. 9, pp. 1–22.
Chen et al. (1975) "Evidence for Hemiacetal Formation", *Biochemistry,* vol. 18, No. 5, pp. 921–925.
Davis et al. (1983) "Leucinal Inhibits . . . ", *Pharmacology Biochemistry Behavior,* vol. 19, pp. 791–794.

(List continued on next page.)

*Primary Examiner*—Jeffrey E. Russel
*Attorney, Agent, or Firm*—Darby & Darby

[57] ABSTRACT

The present invention provides modified amino acids for delivering active agents, and particularly biologically or chemically active agents. The preferred modified amino acids of the present invention include N-acylated or sulfonated amino acids. These modified amino acids are used as carriers to facilitate the delivery of a cargo to a target. Such modified amino acids are well suited to form non-covalent mixtures with biologically-active agents for oral administration to animals. Methods for the preparation and administration of the modified amino acids and compositions including the same are also provided.

30 Claims, No Drawings

U.S. PATENT DOCUMENTS

| | | | |
|---|---|---|---|
| 4,348,384 | 9/1982 | Horikoshi et al. | 424/101 |
| 4,351,337 | 9/1982 | Sidman | 128/260 |
| 4,352,883 | 10/1982 | Lim | 435/178 |
| 4,357,259 | 11/1982 | Senyei et al. | 252/316 |
| 4,388,304 | 6/1983 | Nyeki et al. | 424/177 |
| 4,393,192 | 7/1983 | Curatolo et al. | 528/292 |
| 4,402,856 | 9/1983 | Schnoring et al. | 428/402.22 |
| 4,402,968 | 9/1983 | Martin | 424/273 |
| 4,405,598 | 9/1983 | Brown | 424/45 |
| 4,442,090 | 4/1984 | Kakeya et al. | 424/178 |
| 4,446,138 | 5/1984 | Pack | 424/248.57 |
| 4,450,150 | 5/1984 | Sidman | 424/1.1 |
| 4,457,907 | 7/1984 | Porter | 424/7.1 |
| 4,460,563 | 7/1984 | Calanchi | 424/35 |
| 4,462,839 | 7/1984 | McGinley et al. | 106/198 |
| 4,462,991 | 7/1984 | Higuchi et al. | 424/177 |
| 4,473,620 | 9/1984 | Wu et al. | 428/402.24 |
| 4,483,807 | 11/1984 | Asano | 264/22 |
| 4,492,684 | 1/1985 | Goosen et al. | 424/19 |
| 4,518,433 | 5/1985 | McGinley et al. | 106/180 |
| 4,590,265 | 5/1986 | Bogan et al. | 536/63 |
| 4,608,278 | 8/1986 | Frank | 427/213.35 |
| 4,613,500 | 9/1986 | Suzuki et al. | 429/85 |
| 4,647,455 | 3/1987 | De Bold | 424/95 |
| 4,666,641 | 5/1987 | Fickat et al. | 264/4.3 |
| 4,671,954 | 6/1987 | Goldberg | 424/450 |
| 4,673,566 | 6/1987 | Goosen et al. | 424/19 |
| 4,683,092 | 7/1987 | Tsang | 264/4.3 |
| 4,690,786 | 9/1987 | Ninomiya et al. | 264/4.6 |
| 4,692,284 | 9/1987 | Braden | 264/4.3 |
| 4,692,433 | 9/1987 | Hostetler et al. | 514/12 |
| 4,703,042 | 10/1987 | Bodor | 514/56 |
| 4,708,952 | 11/1987 | Salatinjants | 514/158 |
| 4,745,161 | 5/1988 | Saudek et al. | 525/420 |
| 4,753,804 | 6/1988 | Iaccheri et al. | 424/491 |
| 4,757,007 | 7/1988 | Satoh | 435/69 |
| 4,757,024 | 7/1988 | Roper | 436/507 |
| 4,757,066 | 7/1988 | Shiokari et al. | 514/210 |
| 4,766,012 | 8/1988 | Valenti | 427/213.36 |
| 4,774,320 | 9/1988 | Tagliabue et al. | 530/328 |
| 4,789,734 | 12/1988 | Pierschbacher | 530/395 |
| 4,835,312 | 5/1989 | Itoh et al. | 564/205 |
| 4,837,381 | 6/1989 | Steber et al. | 424/502 |
| 4,844,904 | 7/1989 | Hamaguchi et al. | 424/450 |
| 4,873,087 | 10/1989 | Morishita et al. | 424/433 |
| 4,878,942 | 11/1989 | Motegi et al. | 71/109 |
| 4,886,663 | 12/1989 | Houghten | 424/88 |
| 4,895,725 | 1/1990 | Kantor et al. | 424/455 |
| 4,897,444 | 1/1990 | Brynes et al. | 525/54.1 |
| 4,900,730 | 2/1990 | Miyauchi | 514/12 |
| 4,908,233 | 3/1990 | Takizawa et al. | 427/213.35 |
| 4,919,939 | 4/1990 | Baker | 424/493 |
| 4,925,673 | 5/1990 | Steiner et al. | 424/455 |
| 4,927,928 | 5/1990 | Shroot et al. | 544/154 |
| 4,963,364 | 10/1990 | Fox et al. | 424/455 |
| 4,976,968 | 12/1990 | Steiner | 424/491 |
| 4,983,402 | 1/1991 | Steiner | 424/491 |
| 4,996,292 | 2/1991 | Fox et al. | 528/328 |
| 5,019,400 | 5/1991 | Gombotz et al. | 424/497 |
| 5,023,374 | 6/1991 | Simon | 564/152 |
| 5,039,481 | 8/1991 | Pacifici et al. | 422/4 |
| 5,041,291 | 8/1991 | Bader et al. | 424/426 |
| 5,055,300 | 10/1991 | Gupta | 424/409 |
| 5,066,487 | 11/1991 | Morelle et al. | 424/68 |
| 5,067,961 | 11/1991 | Kelman et al. | 623/5 |
| 5,069,936 | 12/1991 | Yen | 427/213.33 |
| 5,077,278 | 12/1991 | Hafner et al. | 514/30 |
| 5,100,669 | 3/1992 | Hyon et al. | 424/426 |
| 5,100,918 | 3/1992 | Sunshine et al. | 514/557 |
| 5,122,367 | 6/1992 | Ron et al. | 424/80 |
| 5,126,147 | 6/1992 | Silvestri et al. | 424/497 |
| 5,137,892 | 8/1992 | Chu et al. | 514/278 |
| 5,186,947 | 2/1993 | Goettsche et al. | 424/638 |
| 5,204,099 | 4/1993 | Barbier et al. | 424/401 |
| 5,206,384 | 4/1993 | Shibahara et al. | 548/537 |
| 5,216,124 | 6/1993 | Hansen, Jr. et al. | 530/317 |
| 5,244,653 | 9/1993 | Berke et al. | 424/70 |
| 5,250,236 | 10/1993 | Gasco | 264/4.4 |
| 5,271,934 | 12/1993 | Goldberg et al. | 424/401 |
| 5,271,961 | 12/1993 | Mathiowitz et al. | 427/213.31 |
| 5,278,148 | 1/1994 | Branca et al. | 514/19 |
| 5,310,535 | 5/1994 | Kruper, Jr. et al. | 424/1.53 |
| 5,328,992 | 7/1994 | Peter et al. | 534/116 |
| 5,352,461 | 10/1994 | Feldstein et al. | 424/493 |
| 5,384,133 | 1/1995 | Boyes et al. | 424/501 |
| 5,389,377 | 2/1995 | Chagnon et al. | 424/450 |
| 5,389,379 | 2/1995 | Dirix et al. | 424/451 |
| 5,401,516 | 3/1995 | Milstein et al. | 424/491 |
| 5,418,010 | 5/1995 | Janda et al. | 427/213.31 |
| 5,439,686 | 8/1995 | Desai et al. | 424/451 |
| 5,443,841 | 8/1995 | Milstein et al. | 424/451 |
| 5,447,728 | 9/1995 | Milstein et al. | 424/490 |
| 5,451,410 | 9/1995 | Milstein et al. | 424/490 |
| 5,474,997 | 12/1995 | Gray et al. | 514/252 |
| 5,536,813 | 7/1996 | Charpenel et al. | 530/324 |
| 5,540,939 | 7/1996 | Milstein et al. | 424/491 |
| 5,541,155 | 7/1996 | Leone-Bay et al. | 514/2 |
| 5,578,323 | 11/1996 | Milstein et al. | 424/499 |
| 5,601,846 | 2/1997 | Milstein et al. | 424/499 |
| 5,629,020 | 5/1997 | Leone-Bay et al. | 424/489 |
| 5,643,957 | 7/1997 | Leone-Bay et al. | 514/563 |
| 5,650,386 | 7/1997 | Leone-Bay et al. | 514/2 |
| 5,665,700 | 9/1997 | Cho et al. | 514/2 |
| 5,667,806 | 9/1997 | Kantor | 424/484 |
| 5,693,338 | 12/1997 | Milstein | 424/451 |
| 5,705,529 | 1/1998 | Matyus et al. | 514/541 |
| 5,709,861 | 1/1998 | Santiago et al. | 424/184.1 |
| 5,714,167 | 2/1998 | Milstein et al. | 424/490 |
| 5,750,147 | 5/1998 | Kantor | 424/491 |

FOREIGN PATENT DOCUMENTS

| | | | |
|---|---|---|---|
| 0 467 389 | 1/1992 | European Pat. Off. | A61K 9/52 |
| 0 490 549 A1 | 6/1992 | European Pat. Off. | A61K 47/12 |
| 0 517 211 A1 | 9/1992 | European Pat. Off. | A61K 47/12 |
| 0 616 799 A1 | 9/1994 | European Pat. Off. | A61K 7/00 |
| 1 351 358 | 3/1964 | France . | |
| 1 468 601 | 2/1967 | France . | |
| 2 133 926 | 12/1972 | France | A61K 27/00 |
| 2 326 934 | 5/1977 | France | A61K 47/00 |
| 2 565 102 | 12/1985 | France | A61K 9/52 |
| 2 424 169 | 12/1974 | Germany | A61K 9/00 |
| 2 343 037 | 3/1975 | Germany . | |
| 3 202 255 | 1/1982 | Germany | C08L 89/00 |
| 3 612 102 | 10/1986 | Germany | C07K 15/00 |
| 71258/2 | 12/1987 | Israel . | |
| 48-24246 | 3/1973 | Japan . | |
| 56-68612 | 6/1981 | Japan | A61K 31/19 |
| 58-35111 | 3/1983 | Japan | A61K 9/66 |
| 6-107682 | 4/1994 | Japan . | |
| 280825 | 12/1964 | Netherlands . | |
| 280826 | 12/1964 | Netherlands . | |
| B-146698 | 11/1982 | Norway | A61K 37/26 |
| 929401 | 6/1963 | United Kingdom . | |
| 1 075 952 | 7/1967 | United Kingdom . | |
| 1 236 885 | 6/1971 | United Kingdom . | |
| 1 567 763 | 5/1980 | United Kingdom | A61K 9/22 |
| 2 095 994 | 10/1982 | United Kingdom | A61K 9/00 |
| WO 85/00105 | 1/1985 | WIPO | A61K 9/52 |
| WO 85/00110 | 1/1985 | WIPO | A61K 47/00 |
| WO 85/00809 | 2/1985 | WIPO | C07D 233/64 |
| WO 85/02772 | 7/1985 | WIPO | A61K 49/00 |
| WO 87/04076 | 7/1987 | WIPO | A61K 45/02 |

| | | | |
|---|---|---|---|
| WO 88/01213 | 2/1988 | WIPO | B23B 5/16 |
| WO 92/19263 | 12/1992 | WIPO | A61K 39/00 |
| WO 93/18754 | 9/1993 | WIPO | A61K 9/16 |
| WO 93/25583 | 12/1993 | WIPO | C07K 15/00 |
| WO 94/11015 | 5/1994 | WIPO | A61K 37/00 |
| WO 94/14420 | 7/1994 | WIPO | A61K 9/16 |
| WO 94/18950 | 9/1994 | WIPO | A61K 9/127 |
| WO 94/18997 | 9/1994 | WIPO | A61K 37/00 |
| WO 94/21234 | 9/1994 | WIPO | A61K 7/00 |
| WO 94/23702 | 10/1994 | WIPO | A61K 9/16 |
| WO 94/23767 | 10/1994 | WIPO | A61L 9/16 |
| WO 94/24291 | 10/1994 | WIPO | A61K 39/015 |
| WO 94/28878 | 12/1994 | WIPO | A61K 9/14 |
| WO 95/11690 | 5/1995 | WIPO | A61K 37/00 |
| WO 95/28838 | 11/1995 | WIPO | A01N 37/46 |
| WO 95/28920 | 11/1995 | WIPO | A61K 31/19 |
| WO 96/12473 | 5/1996 | WIPO | A61K 9/16 |
| WO 96/12474 | 5/1996 | WIPO | A61K 9/16 |
| WO 96/12475 | 5/1996 | WIPO | A61K 9/16 |
| WO 96/21464 | 7/1996 | WIPO | A61K 39/00 |
| WO 96/30036 | 10/1996 | WIPO | A61K 38/00 |
| WO 96/33699 | 10/1996 | WIPO | A61K 9/16 |
| WO 96/39835 | 12/1996 | WIPO | A01N 43/50 |
| WO 96/40070 | 12/1996 | WIPO | A61K 9/14 |
| WO 96/40076 | 12/1996 | WIPO | A61K 9/16 |
| WO 97/10197 | 3/1997 | WIPO | C07C 51/10 |
| WO 97/31938 | 9/1997 | WIPO | C07K 5/00 |
| 94/23767 | 10/1997 | WIPO . | |
| WO 97/36480 | 10/1997 | WIPO | A01N 37/12 |
| WO 97/47288 | 12/1997 | WIPO . | |

OTHER PUBLICATIONS

Dose, K. (1974) *Origins of Life,* vol. 5, pp. 239–252.
Fasman et al. (1964) *Biochemistry,* vol. 3, No. 11, pp. 1665–1674.
Fox, S. W. et al. (1976) *BioSystems,* vol. 8, pp. 40–44.
Fox, S. W. et al., *Molecular Evolution and the Origin of Life,* Maxel Decker, New York (1977).
Fox, S. W. et al. (1968) *Biochim. Biophys. Acta,* vol. 160, pp. 246–249.
Fox, S. W. (1976) *Origins of Life,* vol. 7, pp. 49–68.
Fox, S. W. (1980) *Naturwissenschaften,* vol. 67, pp. 378–383.
Fox, S. W. et al. (1960) *Archives of Biochemistry and Biophysics,* vol. 86, pp. 281–285.
Fox, S. W. et al. (1974) *Origins of Life,* vol. 5, pp. 227–237.
Fox, S. W. (1984) *Origins of Life,* vol. 14, pp. 485–488.
Gol'dovskii, A.M. (1978) *Zhurnal Evolyutsionnoi Biokhimii i Fiziologii,* vol. 14(6), pp. 437–439.
Gurrieri, S. et al. (1973) *Thermochimica Acta,* vol. 7, pp. 231–239.
Harada, K. et al. (1979) *BioSystems,* vol. 11, pp. 47–53.
Harada et al., (1960) *Archives of Biochemistry and Biophysics,* vol. 86, pp. 274–280.
Hare (1970) *Etude Cenetique De La Polycondsensation Thermique D'$_x$–Amino Acides,* vol. 45, pp. 330–339.
Heinrich, M.R. et al. (1969) *Archives of Biochemistry and Biophysics,* vol. 130, pp. 441–448.
Heinz, B. et al. (1981) *BioSystems,* vol. 14, pp. 33–40.
Hennon, G. et al. (1975) *Biochimie,* vol. 57, pp. 1395–1396.
Hsu, L.L. et al. (1976) *BioSystems,* vol. 8, pp. 89–101.
Hsu, L.L. et al. (1971) *Currents in Modern Biology,* vol. 4, pp. 12–25.
Ishima, Y. et al. (1981), *BioSystems,* vol. 14, pp. 243–251.
Jackson et al. (1991) "Pharmacological . . . ", *J. Pharm. & Exp. Thera.,* vol. 261, No. 1, pp. 546–552.
Jungck, J.R. et al. (1973) *Naturwissenschaften,* vol. 60, pp. 425–427.

Kokufuta, E. et al. (1984) *BioSystems,* vol. 16, pp. 175–181.
Krampitz, G. et al. (1967) *Naturwissenschaften,* pp. 516–517, (1968) pp. 345–346, (1966) pp. 7 and 8.
Lacey, Jr., J.C. et al. (1979) *BioSystems,* vol. 11, pp. 1–7, pp. 9–17.
Martinez Luque–Romero, M. et al. (1986) *BioSystems,* vol. 19, pp. 267–272.
Masinovsky, Z. et al. (1989) *BioSystems,* vol. 22, pp. 305–310.
Matsuno, K. (1982) *BioSystems,* vol. 15, pp. 1–11, (1984) vol. 17, pp. 11–14, (1981) vol. 14, pp. 163–170.
McAlhaney, W.W. et al. (1976) *BioSystems,* vol. 8, pp. 45–50.
Melius, P. et al. (1987) *BioSystems,* vol. 20, pp. 213–217, (1979) vol. 11, pp. 125–132.
Melius, P. et al. (1975) *Biorganic Chemistry,* vol. 4, pp. 385–391.
Miquel, J. et al. (1971) *Currents in Modern Biology,* vol. 3, pp. 299–306.
Nakashima, T. et al. (1980) *J. Mol. Evol.,* vol. 15, pp. 161–168.
Nakashima, T. et al. (1981) *Biosystems,* vol. 14, pp. 151–161.
Novak, V.J.A. (1984) *Origins of Life,* vol. 14, pp. 513–522.
Olafsson, P.G. et al. (1971) *Polymer Letters,* vol. 9, pp. 521–528.
Phillips, R.D. et al. (1974) *Int. J. Peptide Protein Res.,* vol. 6, pp. 309–319.
Przybylski, A.T. et al. (1982) *Die Naturwissenschaften,* vol. 69, pp. 561–563.
Przybylski, A.T. et al. (1984) *Applied Biochemistry and Biotechnology,* vol. 10, pp. 301–307.
Przybylski, A.T. (1985) *BioSystems,* vol. 17, pp. 281–288.
Rohlfing, D.L. (1975) *Origins of Life,* vol. 6, pp. 203–209.
Rohlfing, D.L. (1970) *Science,* vol. 169, pp. 998–1000.
Rohlfing, D.L. (1967) *Archives of Biochemistry and Biophysics,* vol. 118, pp. 468–474.
Rohlfing, D.L. et al. *Catalytic Activities of Thermal Polyanhydro–α–Amino Acids,* pp. 373–418, 1969.
Rohlfing, D.L. et al. (1976) *BioSystems,* vol. 8, pp. 139–145.
Ryan, J.W. et al. (1973) *BioSystems,* vol. 5, pp. 115–118.
Saunders, M.A. et al. (1974) *BioSystems,* vol. 6, pp. 81–92.
Snyder, W.D. et al. (1975) *BioSystems,* vol. 7, pp. 222–229.
Sokol, P.E. (1974) *Journal of the American Oil Chemists'sSociety,* vol. 52, pp. 101–102.
Tschager et al. (1988) *Milchwirtschaftliche Berichte,* vol. 95, pp. 79–83.
Vaughan, G. et al. (1987) *BioSystems,* vol. 20, pp. 219–223.
Vol'kenshtein, M. V. (1989) *Molekulyarnaya Biologiya,* vol. 23(1), pp. 23–37.
Waehneldt, T.V. et al. (1968) *Biochim. Biophys. Acta,* vol. 160, pp. 239–245.
Williams et al. (1991) *J. Biol. Chem.,* vol. 266, No. 8, pp. 5182–5190.
Yuki, A. et al. (1969) *Biochemical and Biophysical Research Communications,* vol. 36(4), pp. 657–663.
Zulaski et al. (1983) "New Carboxyalkyl Inhibitors of Brain Enkenphalinase", *J. Med. Chem.,* 26, pp. 60–65.
(1985) *Chemical Abstracts,* vol. No. 105(1), Abstract No. 12027p, vol. No. 102(6), Abstract No. 50870d.
*Chemical Abstract,* vol. 80(9) Abst. No. 52392a (1974).
Bergeron, Raymond J., et al. (1994) "Macromolecular Self–Assembly of Diketopiperazine Tetrapeptides", *Journal of the American Chemical Society,* vol. 116, pp. 8479–8484.

Bergeron, Raymond J., et al. (1993) "A Comparative Study of the Iron–Clearing Properties of Desferrithiocin Analogues With Desferrioxamine B in a Cebus Monkey Model", *Blood,* vol. 81, No. 8, pp. 2166–2173.

Bergeron, Raymond J., et al. (1992) "A Comparison of the Iron–Clearing Properties of 1,2–Dimethyl–3–Hydroxypyrid–4–One, 1,2–Diethyl–3–Hydroxypyrid–4–One, and Deferoxamine", *Blood,* vol. 79, No. 7, pp. 1882–1890.

Bergeron, Raymond J., et al. (1991) "Evaluation of Desferrithiocin and Its Synthetic Analogs as Orally Effective Iron Chelators", *Journal of Medicinal Chemistry,* vol. 34, No. 7, pp. 2072–2078.

Bergeron, Raymond et al., "A Comparative Evaluation of Iron Clearance Models", *Annals New York Academy of Sciences,* pp. 278–393, Mar. 13–15, 1990.

Andriuoli, G., et al. (1990), *Haemostasis* 20 (suppl. 1):154–158.

Caramazza, I., et al. (1991), *Thrombosis Research* 62:785–789.

Guarini, S., et al. (1983), *Experimentia* 41:350–352.

Guarini, S., et al. (1985), *Pharmacological Research Communications* 17(8):685–697.

Dal Pozzo, A., et al. (1989), *Thrombosis Research* 56:119–124.

Gelb, R., et al (1983), *Lite Sciences* 33(1):83–85.

Watterberg et al. (1988), *Pediatric Research,* vol. 23, No. 4, part 2, p. 570A, column 1, abstract No. 2209.

Bernstein (1985), *Chest* 87(1):68S–73S.

Damge et al. (1988), *Diabetes* 37:246–251.

*Chemical Abstracts*:83 184360k, (1975).

Amino, Y., et al., *Chem. Pharm. Bull.* 36(11):4426–4434 (1988).

Baughman, R.A. et al., *Proc. of the 6th Inter'l. Symp. on Recent Advs. in Drug Delivery Systems,* Ctr. for Controlled Chem. Delivery, University of Utah, Feb. 22–25, 1993, Salt Lake City, UT, pp. 179–180 "Method for Assessing The Stability of Proteinoid Microspheres".

Haas, S. et al., "Assessment Of Stability Of Proteinoid Microspheres", *Proceed. Intern. Symp. Control. Rel. Bioact. Mater.,* 20 (1993), Controlled Release Society, Inc.

X. Ma, et al., *Proceed. Intern. Symp. Control. Rel. Bioact. Mater.,* 20(1993), Controlled Release Society, Inc. "In Vitro Mechanistic Investigation of the Proteinoid Microsphere Oral Delivery System".

Yen, H.–R H., et al., "Adsorption of Sulforhodamine 101 on Proteinoid Microspheres" *Proceed. Intern. Symp. Control. Rel. Bioact. Mater.,* 20 (1993), Controlled Release Society, Inc.

Presented at *"IBC Rational Drug Design Conference",* San Diego, Calif.—Dec. 1994.

Leone–Bay et al., Presented at *"Winter Conference on Medicinal and Bioorganic Chemistry"* Steamboat Springs, Colorado—Feb. 1995 "Microsphere Formation and Drug Delivery in a Series of Derivatized Amino Acids".

Santiago et al., *Pharm. Res.* 11: 1994, p. S–298 "Oral Delivery of Heparin Microspheres made with modified Amino Acids".

Leone–Bay et al., *Pharm. Res.* 11: 1994, p. S–121 "Oral Delivery of Heparin using Acylated Amino Acids".

Sarubbi et al., *Pharm. Res.* 11: 1994, p. S–299 "Oral Calcitonin Delivery using the PODDS Technology".

Leipold et al., *Pharm. Res.* 11: 1994, p. S–298 "Oral Delivery of Interferon in Rats and Primates".

Santiago et al., *Pharm. Res.* 11: 1994, p. S–298 "Evaluation in Rats of Vehicles for the Oral Delivery of Low Molecular Weight Heparin".

X. Ma et al., PDD 7303 *Pharmaceutical Research* 9(10):S–244, 1992 (Oct. Supplement).

Milstein et al., *Symposia Abstracts.* AAPS Annual Meeting, San Antonia, TX, Nov. 15–19, 1993.

Santiago et al. "Initial Studies In The Assessment of Proteinoid Microsphere Activity" *Proceed. Intern. Symp. Control. Rel. Bioact. Mater.,* 20 (1993), Controlled Release Society, Inc.

Santiago et al. "Oral Immunization of Rats with Influenza Virus M Protein (M1) Microspheres" *Proceed. Intern. Symp. Control. Rel. Bioact. Mater.,* 19 (1992), Controlled Release Society, Inc., p. 116–117.

Santiago et al. "Proteinoid Microspheres For the Oral Delivery of Heparin" *Proceed. Intern. Symp. Control. Rel. Bioact. Mater.,* 19 (1992), Controlled Release Society, Inc. p. 514–515.

Santiago et al. *American Society for Microbiology* 92nd General Meeting, Abstract of the General Meeting, p. 159, May 26–30, 1992.

Milstein et al. "Preparation And In Vitro Characterization Of Proteinoid Microspheres" *Proceed. Intern. Symp. Control. Rel. Bioact. Mater.,* 19 (1992), Controlled Release Society, Inc. p. 516–517.

Doris K. Chiappetta, *Eastern Analytical Symposium,* Nov. 17, 1992 "Solutions for Problems in Bioanalysis".

Elizabeth A. Harris M.S., *Eastern Analytical Symposium,* Nov. 17, 1992 "Solutions for Problems in Bioanalysis".

*AAPS 6th Ann. Meeting and Expo.,* "Proteinoids—A Novel Drug Delivery System" Nov. 19, 1992, p. 33.

Milstein et al., "Efficient Oral Delivery Of Monoclonal Antibodies By Proteinoid Encapsulation" The 1993 Miami Bio–Technology Winter Symposium—Advances in Gene Technology: Protein Engineering and Beyond, Jan. 17–22, 1993.

Xinghang Ma, et al. "Stability Study of Drug–loaded Proteinoid Microsphere Formulations during Freeze–drying" *Journal of Drug Targeting,* 1994, vol. 2, pp. 9–21.

Baughman et al., "Screening Candidate Microsphere Formulations By Incubating In Simulated Digestive Fluids" *Proc. of the 6th Intern'l Sympo. on Recent Advances in Drug Delivery Systems,* Ctr. for Controlled Chem. Delivery, University of Utah, Feb. 22–25, 1993, pp. 181–182.

Robert O. Dillman, M.D., *Annals of Internal Medicine* 1989:111 pp. 592–600, "Monoclonal Antibodies for Treating Cancer".

Brendan D. Curti, *Critical Reviews in Oncology/Hematology,* 1993: 14 pp. 29–39 "Physical barriers to drug delivery in tumors".

V. Hird et al, *Genes and Cancer,* edited by Desmond Carney & Karol Sikora, pp. 183–189, Immunotherapy with Monoclonal Antibodies. (Not dated).

Michael E. Osband et al., *Immunology Today,* vol. 11, No. 6 1990, pp. 193–195, "Problems in the investigational study and clinical use of cancer immunotherapy".

William J. Harris, *Tibtech* Feb. 1993, vol. 11, pp. 42–44 "Therapeutic antobodies—the coming of age".

Thomas A. Waldmann, *Science,* Jun. 21, 1991, 252:1657–1662, "Monoclonal Antibodies in Diagnosis and Therapy".

*Chemical Abstracts,* 76(14):72994u, (1971).

*Chemical Abstracts,* 84(7):44660d, (1975).

*Chemical Abstracts,* 86(16):107529g, (1976).

*Chemical Abstracts*, 112(15):134663h, (1989).
*Chemical Abstracts*, 114(22):214519x, (1990).
J. Györe et al., *Thermal Analysis*, vol. 2—Proceeding Fourth ICTA Budapest 1974, p. 387–394.
*Chemical Abstracts*, 99(19) 158832b, (1982).
*Derwent Abstracts*, JP 67008622, (1967).
*Journal of Medicinal Chemistry*, vol. 38, No. 21, pp. 4257–4262, (1995), "Microsphere Formation in a Series of Derivatized α–Amino Acids: Properties, Molecular Modeling, and Oral Delivery of Salmon Calcitonin".
Aldrea Leone–Bay et al., *Journal of Medicinal Chemistry*, vol. 38, No. 21, pp. 4263–4269, (1995), "N–Acylated α–Amino Acids as Novel Oral Delivery Agents for Proteins".
*The Extra Pharmacopoeia*, Thirtieth Edition, pp. 325–326, (1993).
Stephen J. Douglas et al., *Chemistry and Industry*, vol. 22: 748–751, 1985.
C.A. Finch, *Chemistry and Industry*, vol. 22: 752–756, 1985.
John A. Butera et al., *J. Med. Chem.*, vol. 34: 3212–3228, 1990.
Madeline G. Cimini et al., *Ann. Report in Med Chem.*, vol. 27:89–98., 1992.
Bernadette Earley et al., *Brain Research*, vol. 546:282–286, 1991.
John W. Ellingboe et al., *J. Med. Chem.*, vol. 35:705–716, 1992.
William C. Lumma et al., *J. Med. Chem.*, vol. 30:758–763, 1987.
Joseph J. Lynch et al., *J. of Pharm. and Exp. Therap.*, vol. 269:541–554, 1994.
Kiyoshi Matsuno et al., *Brain Research*, vol. 575:315–319, 1992.
Thomas K. Morgan et al., *J. Med. Chem.*, vol. 33:1091–1097, 1990.
Hitoshi Oinuma et al., *J. Med Chem.*, vol. 33:903–905, 1990.
Tadimeti S. Rao et al., *Molecular Pharmacology*, vol. 37:978–982, 1990.
Asaji Kondo, *Microcapsule Processing and Technology*, pp. 154–165, 1979.
G. Pastores et al., *J. Liquid Chromatography*, 18(15):3049–3059, 1995.
D. Sinha et al., *J. Bio. Chem.*, 260(19):10714–10719. 1985.
E. Franssen et al., *J. Med. Chem.*, 35:1246–1259, 1992.
*Chemical Abstracts*, 99(23):191473h, Dec. 5, 1983.
R. Langer, *Science*, 249:1528, Sep. 28. 1990.
A. Alonso et al., *Vaccine*, 12:299, 1994.
A. Leone–Bay et al., *J. Med. Chem.*, 39:2571–2578, 1996.
R. Thompson, *Biochemistry*, 12:47–51, 1973.
S. Thompson, *J. Med. Chem.*, abstract, 86:174780, 1986.
Morrison et al. Organic Chemistry Boston: Allyn and Bacon, Inc. pp. 671–672, 755–758, 1973.
Chemical Abstracts, Registry No. 73548–12–6 (Apr. 1991).
Chemical Abstracts, Registry No. 70204–54–5 (Apr. 1991).
G. Picciola, *Il Farmaco*, 31:655–664 (1976).

MODIFIED AMINO ACIDS AND COMPOSITIONS COMPRISING THE SAME FOR DELIVERING ACTIVE AGENTS

This is a continuation of application Ser. No. 08/414,654, filed Mar. 31, 1995 now U.S. Pat. No. 5,650,386.

FIELD OF THE INVENTION

The present invention relates to compounds for delivering active agents, and particularly biologically or chemically active agents such as, for example, bioactive peptides and the like. These compounds are used as carriers to facilitate the delivery of a cargo to a target. The carriers are modified amino acids and are well suited to form non-covalent mixtures with biologically-active agents for oral administration to animals. Methods for the preparation and for the administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself.

Biologically or chemically active agents are particularly vulnerable to such barriers. For example in the delivery to animals of pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically or chemically active agents would be the route of choice for administration to animals if not for biological, chemical, and physical barriers such as varying pH in the gastro-intestinal (GI) tract, powerful digestive enzymes, and active agent impermeable gastrointestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastro-intestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters,* Vol. 62, pg. 60; and Hashimoto et al. (1979), *Endocrinology Japan,* Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents.

SUMMARY OF THE INVENTION

Compositions which are useful in the delivery of active agents are provided. These compositions include at least one active agent, and preferably a biologically or chemically active agent, and at least one of the following compounds I–XXXV.

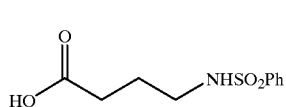

I

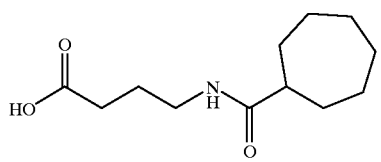

II

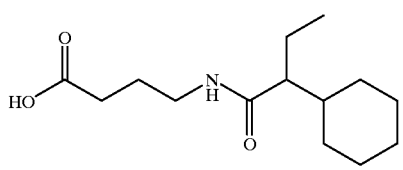

III

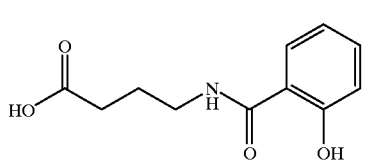

IV

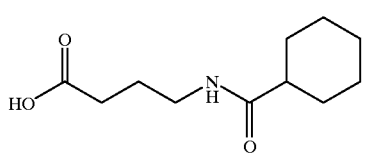

V

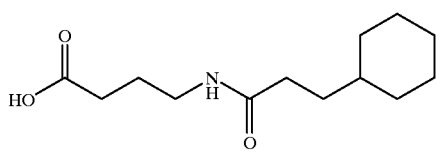

VI

VII
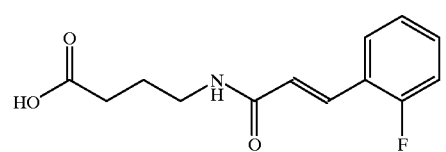
VIII
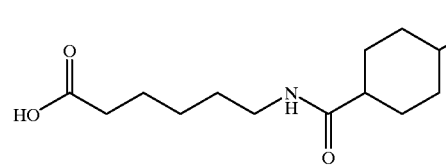
IX
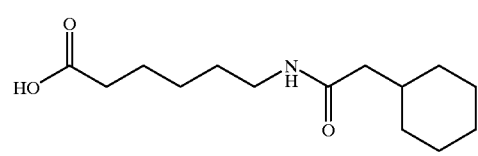
X
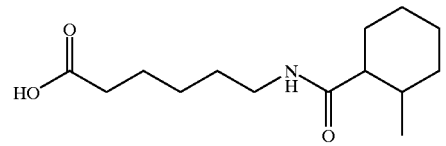
XI
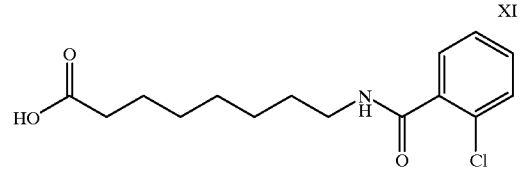
XII
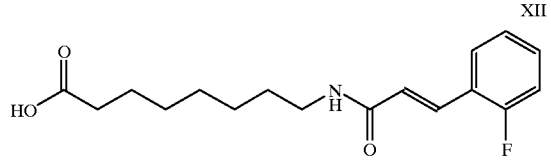
XIII
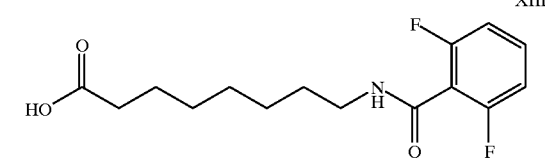
XIV
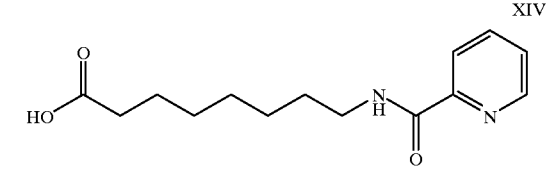
XV
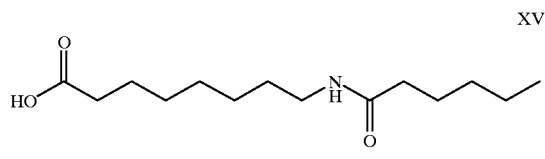
XVI
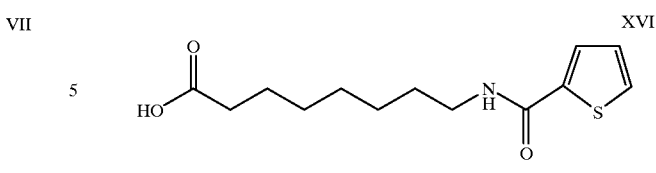
XVII
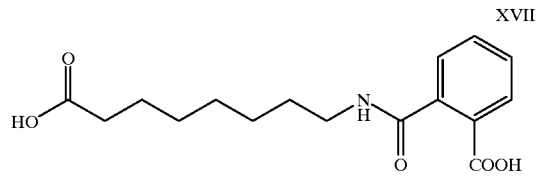
XVIII
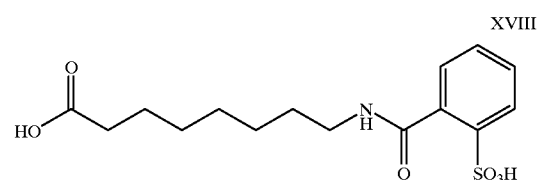
XIX
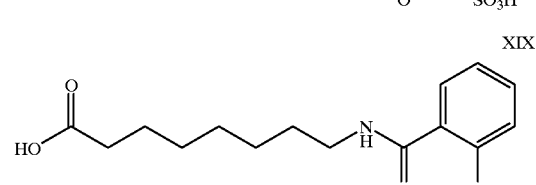
XX
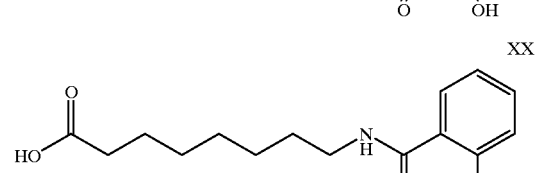
XXI
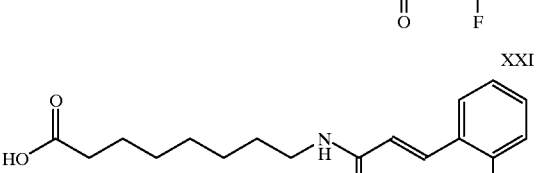
XXII
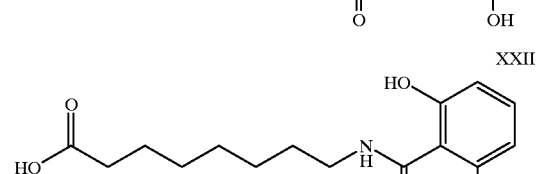
XXIII
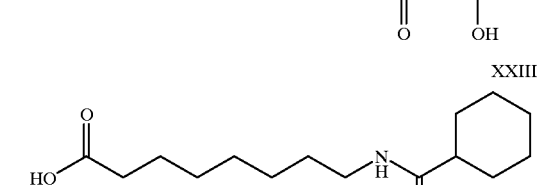
XXIV

-continued

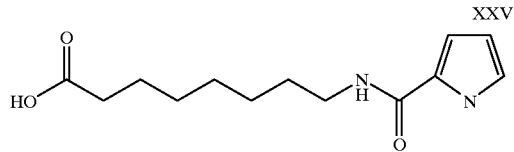
XXV

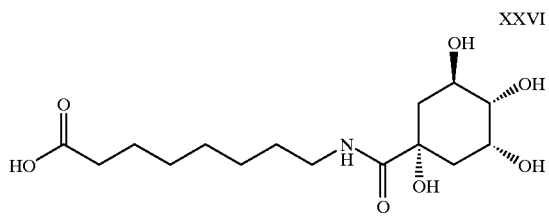
XXVI

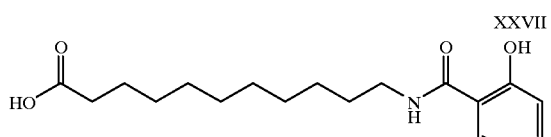
XXVII

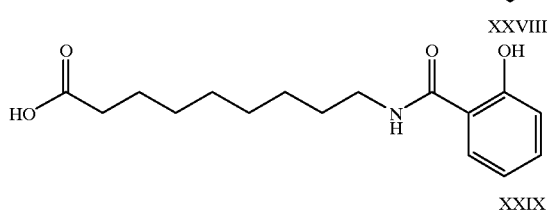
XXVIII

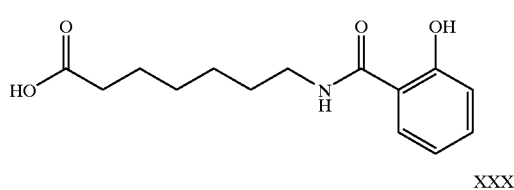
XXIX

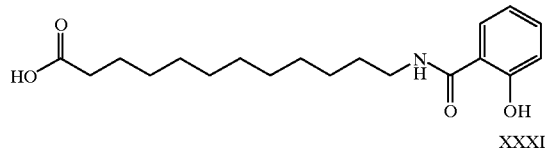
XXX

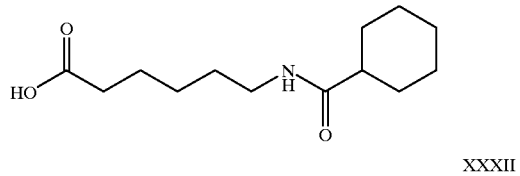
XXXI

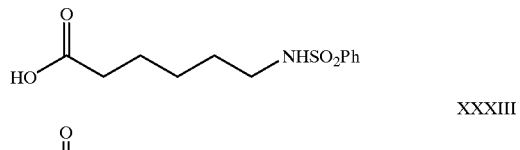
XXXII

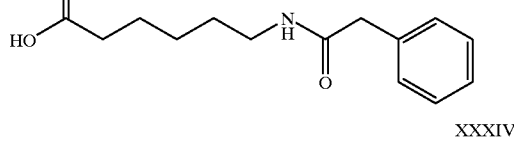
XXXIII

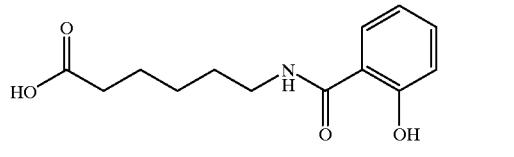
XXXIV

-continued

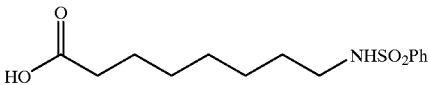
XXXV or salts thereof.

Further contemplated by the present invention are dosage unit forms that include these compositions.

Also contemplated is a method for preparing these compositions which comprises mixing at least one active agent with at least one compound as described above, and optionally, a dosing vehicle.

In an alternative embodiment, these non-toxic compounds are orally administered to animals as part of a delivery system by blending or mixing the compounds with an active agent prior to administration.

Further provided is a method for the preparation of a compound having the formula

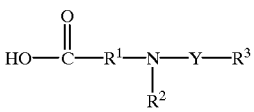
XXXVI wherein Y is

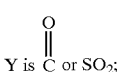

Y is C or $SO_2$;

$R^1$ is $C_3$–$C_{24}$ alkyl, $C_2$–$C_{20}$ alkenyl, $C_2$–$C_{20}$ alkyne, cycloalkyl, or aromatic;

$R^2$ is hydrogen, $C_1$–$C_4$ alkyl, or $C_2$–$C_4$ alkenyl; and $R^3$ is $C_1$–$C_7$ alkyl, $C_3$–$C_{10}$ cycloalkyl, aryl, thienyl, pyrrolo, or pyridyl, where $R^3$ is optionally substituted by one or more $C_1$–$C_5$ alkyl group, $C_2$–$C_4$ alkenyl group, F, Cl, OH, $SO_2$, COOH, or $SO_3H$; said method comprising (a) reacting in water and the presence of a base, a compound having the formula

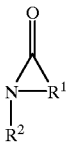
XXXVII with a compound having the formula

wherein Y, $R^1$, $R^2$, and $R^3$ are as above and X is a leaving group.

DETAILED DESCRIPTION OF THE INVENTION

The specific compositions of the present invention include an active agent and a modified amino acid. These compositions may be used to deliver various active agents through various biological, chemical, and physical barriers and are particularly suited for delivering active agents which are subject to environmental degradation. The compositions of the subject invention are particularly useful for delivering or administering biologically or chemically active agents to any animals such as birds; mammals, such as primates and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Active Agents

Active agents suitable for use in the present invention include biologically or chemically active agents, chemically active agents, including, but not limited to, fragrances, as well as other active agents such as, for example, cosmetics.

Biologically or chemically active agents include, but are not limited to, pesticides, pharmacological agents, and therapeutic agents. For example, biologically or chemically active agents suitable for use in the present invention include, but are not limited to, peptides, and particularly small peptides; hormones, and particularly hormones which by themselves do not or only pass slowly through the gastro-intestinal mucosa and/or are susceptible to chemical cleavage by acids and enzymes in the gastro-intestinal tract; polysaccharides, and particularly mixtures of mucopolysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); anti-microbials, including, but not limited to anti-fungal agents; or any combination thereof.

Modified Amino Acids

The terms modified amino acid, modified poly amino acid, and modified peptide are meant to include amino acids which have been modified, or poly amino acids and peptides in which at least one amino acid has been modified, by acylating or sulfonating at least one free amine group with an acylating or sulfonating agent which reacts with at least one of the free amine groups present.

Amino acids, poly amino acids, and peptides, in modified form, may be used to deliver active agents including, but not limited to, biologically or chemically active agents such as for example, pharmacological and therapeutic agents.

An amino acid is any carboxylic acid having at least one free amine group and includes naturally occurring and synthetic amino acids.

Poly amino acids are either peptides or two or more amino acids linked by a bond formed by other groups which can be linked, e.g. an ester, anhydride, or an anhydride linkage.

Peptides are two or more amino acids joined by a peptide bond. Peptides can vary in length from dipeptides with two amino acids to poly peptides with several hundred amino acids. See *Chambers Biological Dictionary*, editor Peter M. B. Walker, Cambridge, England: Chambers Cambridge, 1989, page 215. Special mention is made of di-peptides, tri-peptides, tetra-peptides, and penta-peptides.

Although compounds I–XXXV above have been found to act as carriers for the oral delivery of biologically or chemically active agents, special mention is made of compounds I–XXX above.

Modified amino acids are typically prepared by modifying the amino acid or an ester thereof. Many of these compounds are prepared by acylation or sulfonation with agents having the formula

wherein: R⁴ is the appropriate radical to yield the modification indicated in the final product,

and X is a leaving group. Typical leaving groups include, but are not limited to, halogens such as, for example, chlorine, bromine, and iodine. Additionally, the corresponding anhydrides are modifying agents.

Many of the compounds of the present invention can be readily prepared from amino acids by methods within the skill of those in the art based upon the present disclosure. For example, compounds I–VII are derived from aminobutyric acid. Compounds VIII–X and XXXI–XXIIV are derived from aminocaproic acid. Compounds XI–XXVI and XXXV are derived from aminocaprylic acid. For example, the modified amino acid compounds above may be prepared by reacting the single amino acid with the appropriate modifying agent which reacts with free amino moiety present in the amino acids to form amides. Protecting groups may be used to avoid unwanted side reactions as would be known to those skilled in the art.

The amino acid can be dissolved in aqueous alkaline solution of a metal hydroxide, e.g., sodium or potassium hydroxide, and heated at a temperature ranging between about 5° C. and about 70° C., preferably between about 10° C. and about 40° C., for a period ranging between about 1 hour and about 4 hours, preferably about 2.5 hours. The amount of alkali employed per equivalent of $NH_2$ groups in the amino acid generally ranges between about 1.25 and about 3 mmole, preferably between about 1.5 and about 2.25 mmole per equivalent of $NH_2$. The pH of the solution generally ranges between about 8 and about 13, preferably ranging between about 10 and about 12.

Thereafter, the appropriate amino modifying agent is added to the amino acid solution while stirring. The temperature of the mixture is maintained at a temperature generally ranging between about 5° C. and about 70° C., preferably between about 10° C. and about 40° C., for a period ranging between about 1 and about 4 hours. The amount of amino modifying agent employed in relation to the quantity of amino acid is based on the moles of total free $NH_2$ in the amino acid. In general, the amino modifying agent is employed in an amount ranging between about 0.5 and about 2.5 mole equivalents, preferably between about 0.75 and about 1.25 equivalents, per molar equivalent of total $NH_2$ group in the amino acid.

The reaction is quenched by adjusting the pH of the mixture with a suitable acid, e.g., concentrated hydrochloric acid, until the pH reaches between about 2 and about 3. The mixture separates on standing at room temperature to form a transparent upper layer and a white or off-white precipitate. The upper layer is discarded, and the modified amino acid is collected from the lower layer by filtration or decantation. The crude modified amino acid is then dissolved in water at a pH ranging between about 9 and about 13, preferably between about 11 and about 13. Insoluble materials are removed by filtration and the filtrate is dried in vacuo. The yield of modified amino acid generally ranges between about 30 and about 60%, and usually about 45%.

If desired, amino acid esters, such as, for example benzyl, methyl, or ethyl esters of amino acid compounds, may be used to prepare the modified amino acids of the invention. The amino acid ester, dissolved in a suitable organic solvent such as dimethylformamide, pyridine, or tetrahydrofuran is reacted with the appropriate amino modifying agent at a temperature ranging between about 5° C. and about 70° C., preferably about 25° C., for a period ranging between about 7 and about 24 hours. The amount of amino modifying agent used relative to the amino acid ester is the same as described above for amino acids. This reaction may be carried out with or without a base such as, for example, triethylamine or diisopropylethylamine.

Thereafter, the reaction solvent is removed under negative pressure and the ester functionality is removed by hydrolyzing the modified amino acid ester with a suitable alkaline solution, e.g. 1N sodium hydroxide, at a temperature ranging between about 50° C. and about 80° C., preferably about 70° C., for a period of time sufficient to hydrolyze off the ester group and form the modified amino acid having a free carboxyl group. The hydrolysis mixture is then cooled to room temperature and acidified, e.g. aqueous 25% hydrochloric acid solution, to a pH ranging between about 2 and about 2.5. The modified amino acid precipitates out of solution and is recovered by conventional means such as filtration or decantation. Benzyl esters may be removed by hydrogenation in an organic solvent using a transition metal catalyst.

The modified amino acid may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0–500 mM sodium chloride gradient is employed.

In an alternate method modified amino acids having the formula

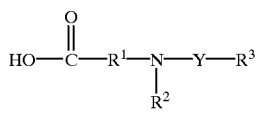

XXXVI wherein Y is

Y is C or SO$_2$;

$R^1$ is $C_3$–$C_{24}$ alkyl, $C_2$–$C_{20}$ alkenyl, $C_2$–$C_{20}$ alkyne, cycloalkyl, or aromatic;

$R^2$ is hydrogen, $C_1$–$C_4$ alkyl, or $C_2$–$C_4$ alkenyl; and $R^3$ is $C_1$–$C_7$ alkyl, $C_3$–$C_{10}$ cycloalkyl, aryl, thienyl, pyrrolo, or pyridyl, where $R^3$ is optionally substituted by one or more $C_1$–$C_5$ alkyl group, $C_2$–$C_4$ alkenyl group, F, Cl, OH, SO$_2$, COOH or, SO$_3$H; may be prepared by (a) reacting in water and the presence of a base a compound having the formula

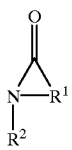

XXXVII with a compound having the formula

$R^3$—Y—X, wherein Y, $R^1$, $R^2$, and $R^3$ are as above and X is a leaving group.

Compound XXXVII can be prepared, for example by the method described in Olah et al., *Synthesis*, 537–538 (1979).

Delivery Systems

The compositions of the present invention may include one or more active agents.

In one embodiment, compounds I–XXXV or poly amino acids or peptides that include at least one of these compounds may be used directly as a delivery carrier by simply mixing one or more compound, poly amino acid or peptide with the active agent prior to administration.

In an alternative embodiment, the compounds, poly amino acids, or peptide may be used to form microspheres containing the active agent. These compounds, poly amino acids, or peptides are particularly useful for the oral administration of certain biologically-active agents, e.g., small peptide hormones, which, by themselves, do not pass or only pass slowly through the gastrointestinal mucosa and/or are susceptible to chemical cleavage by acids and enzymes in the gastrointestinal tract.

If the modified amino acids, poly amino acids, or peptides are to be converted into microspheres, the mixture is optionally heated to a temperature ranging between about 20 and about 50° C., preferably about 40° C., until the modified amino acid(s) dissolve. The final solution contains between from about 1 mg and to about 2000 mg of compound, poly amino acid, or peptide per mL of solution, preferably between about 1 and about 500 mg per mL. The concentration of active agent in the final solution varies and is dependent on the required dosage for treatment. When necessary, the exact concentration can be determined by, for example, reverse phase HPLC analysis.

When the compounds, poly amino acids, or peptides are used to prepare microspheres, another useful procedure is as follows: Compounds, poly amino acids, or peptides are dissolved in deionized water at a concentration ranging between about 75 and about 200 mg/ml, preferably about 100 mg/ml at a temperature between about 25° C. and about 60° C., preferably about 40° C. Particulate matter remaining in the solution may be removed by conventional means such as filtration.

Thereafter, the compound, poly amino acid, or peptide solution, maintained at a temperature of about 40° C., is mixed 1:1 (V/V) with an aqueous acid solution (also at about 40° C.) having an acid concentration ranging between about 0.05N and about 2N, preferably about 1.7N. The resulting mixture is further incubated at 40° C. for a period of time effective for microsphere formation, as observed by light microscopy. In practicing this invention, the preferred order of addition is to add the compound, poly amino acid, or peptide solution to the aqueous acid solution.

Suitable acids for microsphere formation include any acid which does not (a) adversely effect the modified amino acids, poly amino acids, or peptides e.g., initiate or propagate chemical decomposition;

(b) interfere with microsphere formation;

(c) interfere with microsphere incorporation of the active agent cargo; and (d) adversely interact with the active agent cargo.

Preferred acids for use in this aspect include acetic acid, citric acid, hydrochloric acid, phosphoric acid, malic acid and maleic acid.

A microsphere stabilizing additive may be incorporated into the aqueous acid solution or into the compound or cargo solution prior to the microsphere formation process. With some drugs the presence of such additives promotes the stability and/or dispersibility of the microspheres in solution.

The stabilizing additives may be employed at a concentration ranging between about 0.1 and 5% (w/v), preferably about 0.5% (w/v). Suitable, but non-limiting, examples of microsphere stabilizing additives include gum acacia, gelatin, methyl cellulose, polyethylene glycol, carboxylic acid and salts thereof, and polylysine. The preferred stabilizing additives are gum acacia, gelatin and methyl cellulose.

Under the above conditions, the compound molecules, poly amino acids, or peptides form hollow or solid matrix type microspheres wherein the cargo is distributed in a carrier matrix or capsule type microspheres encapsulating liquid or solid cargo. If the compound, poly amino acid, or peptide microspheres are formed in the presence of a soluble material, e.g., a pharmaceutical agent in the aforementioned aqueous acid solution, this material will be encapsulated within the microspheres. In this way, one can encapsulate pharmacologically active materials such as peptides, proteins, and polysaccharides as well as charged organic molecules, e.g., antimicrobial agents, which normally have poor bioavailability by the oral route. The amount of pharmaceutical agent which may be incorporated by the microsphere is dependent on a number of factors which include the concentration of agent in the solution, as well as the affinity of the cargo for the carrier. The compound, poly amino acid, or peptide microspheres do not alter the physiological and biological properties of the active agent. Furthermore, the encapsulation process does not alter the pharmacological properties of the active agent. Any pharmacological agent can be incorporated within the microspheres. The system is particularly advantageous for delivering chemical or biological agents which otherwise would be destroyed or rendered less effective by conditions encountered within the body of the animal to which it is administered, before the microsphere reaches its target zone (i.e., the area in which the contents of the microsphere are to be released) and for delivering pharmacological agents which are poorly absorbed in the gastro-intestinal tract. The target zones can vary depending upon the drug employed.

The particle size of the microsphere plays an important role in determining release of the active agent in the targeted area of the gastro-intestinal tract. The preferred microspheres have diameters between about ≦0.1 microns and about 10 microns, preferably between about 0.5 microns and about 5 microns. The microspheres are sufficiently small to release effectively the active agent at the targeted area within the gastro-intestinal tract such as, for example, between the stomach and the jejunum. Small microspheres can also be administered parenterally by being suspended in an appropriate carrier fluid (e.g., isotonic saline) and injected directly into the circulatory system, intramuscularly or subcutaneously. The mode of administration selected will vary, of course, depending upon the requirement of the active agent being administered. Large amino acid microspheres (>50 microns) tend to be less effective as oral delivery systems.

The size of the microspheres formed by contacting compounds, poly amino acids, or peptides with water or an aqueous solution containing active agents can be controlled by manipulating a variety of physical or chemical parameters, such as the pH, osmolarity or ionic strength of the encapsulating solution, size of the ions in solution and by the choice of acid used in the encapsulating process.

The administration mixtures are prepared by mixing an aqueous solution of the carrier with an aqueous solution of the active ingredient, just prior to administration. Alternatively, the carrier and the biologically or chemically active ingredient can be admixed during the manufacturing process. The solutions may optionally contain additives such as phosphate buffer salts, citric acid, acetic acid, gelatin, and gum acacia.

Stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent is an amount effective to accomplish the purpose of the particular active agent. The amount in the composition typically is a pharmacologically or biologically effective amount. However, the amount can be less than a pharmacologically or biologically effective amount when the composition is used in a dosage unit form, such as a capsule, a tablet or a liquid, because the dosage unit form may contain a multiplicity of carrier/biologically or chemically active agent compositions or may contain a divided pharmacologically or biologically effective amount. The total effective amounts can then be administered in cumulative units containing, in total, pharmacologically or biologically or chemically active amounts of biologically or pharmacologically active agent.

The total amount of active agent, and particularly biologically or chemically active agent, to be used can be determined by those skilled in the art. However, it has surprisingly been found that with some biologically or chemically active agents, the use of the presently disclosed carriers provides extremely efficient delivery. Therefore, lower amounts of biologically or chemically active agent than those used in prior dosage unit forms or delivery systems can be administered to the subject, while still achieving the same blood levels and therapeutic effects.

The amount of carrier in the present composition is a delivery effective amount and can be determined for any particular carrier or biologically or chemically active agent by methods known to those skilled in the art.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

Administration of the present compositions or dosage unit forms preferably is oral or by intraduodenal injection.

The delivery compositions of the present invention may also include one or more enzyme inhibitors. Such enzyme inhibitors include, but are not limited to, compounds such as actinonin or epiactinonin and derivatives thereof. These compounds have the formulas below:

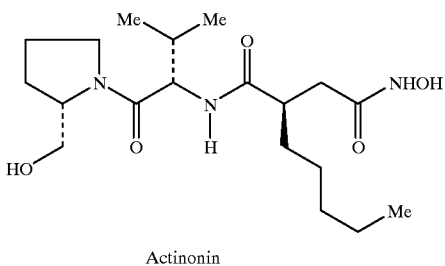

Actinonin

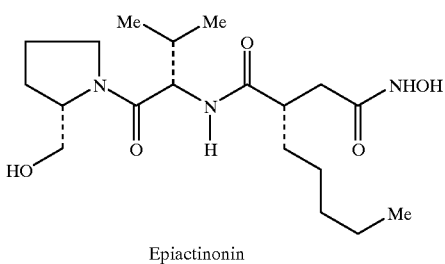

Epiactinonin

Derivatives of these compounds are disclosed in U.S. Pat. No. 5,206,384. Actinonin derivatives have the formula:

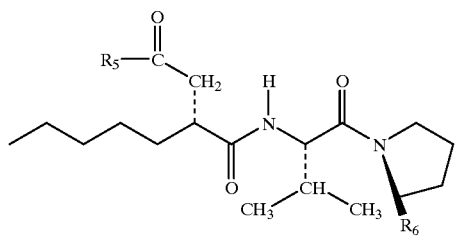

wherein $R^5$ is sulfoxymethyl or carboxyl or a substituted carboxy group selected from carboxamide, hydroxyaminocarbonyl and alkoxycarbonyl groups; and $R^6$ is hydroxyl, alkoxy, hydroxyamino or sulfoxyamino group. Other enzyme inhibitors include, but are not limited to, "TRASYLOL™" (aprotrisins) and Bowman-Birk inhibitor.

The compounds and compositions of the subject invention are useful for administering biologically or chemically active agents to any animals such as birds; mammals, such as primates and particularly humans; and insects. The system is particularly advantageous for delivering chemically or biologically or chemically active agents which would otherwise be destroyed or rendered less effective by conditions encountered before the active agent its target zone (i.e. the area in which the active agent of the delivery composition are to be released) and within the body of the animal to which they are administered. Particularly, the compounds and compositions of the present invention are useful in orally administering active agents, especially those which are not ordinarily orally deliverable.

DESCRIPTION OF THE PREFERRED EMBODIMENTS

The following examples illustrate the invention without limitation. All parts are given by weight unless otherwise indicated.

EXAMPLE 1

Compound XIX was prepared as follows:

A 3 L three-neck round bottom flask was fitted with an overhead mechanical stirrer and a thermometer, and the flask was cooled in an ice-bath. A solution of 8-aminocaprylic acid (100.0 g, 0.65 moles) in 2M aqueous sodium hydroxide (1.4 L) was charged into the round bottom flask. The temperature of the solution was kept at about 5° C., and O-acetylsalicyloyl chloride (198.6 g, 0.76 moles, 1.2 equiv.) was added portionwise over 7 hours. The mixture was stirred at 5° C. for 12 hours to yield a yellow homogenous solution. The solution was acidified with 1M hydrochloric acid to pH 6.8 and was extracted with ethyl acetate (2×600 mL). The pH of the aqueous layer was readjusted to 6.3 and was further extracted with ethyl acetate (2×600 mL). The organic layers were combined, dried over anhydrous sodium sulfate, filtered, and evaporated under reduced pressure. The residue was redissolved in a minimum volume of 2M aqueous sodium hydroxide, and the pH of the solution was between 9.5 and 10. The mixture was acidified with stirring with 1M hydrochloric acid to pH of about 6.2, and a solid was formed. The solid was filtered, washed with water (3×300 mL), and recrystallized from 55% methanol/water (v/v) to yield Compound XVIII as an off-white solid (99.7 g, 57%).

Properties are listed below.

mp 116–117° C. $^1$H NMR (300 MHz, DMSO-$d_6$) δ: 12.70 (1H, br s), 11.95 (1H, br s) 8.81 (1H, t), 7.82 (1H, m), 7.38 (1H, m), 6.84 (2H, m), 2.36 (2H, q), 2.18 (2H, t), 1.50 (4H, br m), 1.28 (6H, m), Anal.

Calcd for $C_{15}H_{21}NO_4$: C, 64.50; H, 7.58;l N, 5.02. Found: C, 64.26; H, 7.81; N, 4.93.

Similar procedures were used to prepare Compounds I, II, III, IV, VI, IX, X, XI, XII, XIII, XIV, XX, XXI, XXIII, XXVII, XXXIII, and XXXIV.

Properties are listed below.

Compound I: $^1$H NMR (300 MHz, $D_2O$): δ 1.5 (2H, m) 2.0 (2H, t) 2.3 (2H, t) 7.5 (2H, t) 7.6 (1H, m) 7.3 (2H, m)

Compound II: $^1$H NMR (300 MHz, $D_2O$): δ 1.4 (8H, m) 1.7 (6H, m) 2.1 (2H, t) 1.25 (1H, m) 3.05 (2H, t)

Compound III: $^1$H NMR (300 MHz, DMSO-$d_6$): δ 0.7 (3H, m) 0.9 (2H, m) 1.1 (3H, q) 1.6 (5H, m) 1.75 (2H, q) 2.1 (2H, t) 3.0 (2H, q) 7.9 (1H, m)

Compound IV: Anal. Calcd for $C_{11}H_{13}NO_4$: C, 59.9, H, 5.87, N, 6.27 Found: C, 58.89, H, 5.85, N, 6.07. $^1$H NMR (300 MHz, DMSO-$d_6$): δ 1.8 (2H, m) 2.3 (2H, t) 3.1 (2H, q) 6.9 (2H, t) 7.4 (1H, t) 7.8 (1H, d) 8.85 (1H, t) 12.0 (1H, s) 12.15 (1H, s)

Compound VI: $^1$H NMR (300 MHz, $D_2O$): δ 0.8 (2H, m) 1.1 (4H, m) 1.4 (2H, q) 1.6 (7H, m) 2.15 (4H, m) 3.1 (2H, t)

Compound IX: $^1$H NMR (300 MHz, DMSO-$d_6$): δ 0.9 (q, 3H), 1.2 (m, 7H), 1.3 (q, 2H) 1.5 (q, 3H), 1.9 (d, 2H), 2.0 (d, 1H), 2.2 (t, 2H), 3.0 (q, 3H), 7.7 (s, 1H), Compound X: $^1$H NMR (300 MHz, DMSO-$d_6$): δ 0.7 (d, 2H), 0.9 (dd, 1H), 1.2–1.3 (m, 7H), 1.5 (q, 3H), 1.6–1.8 (m, 5H), 2.1 5 (t, 2H), 3. 0 (m, 3H), 7.5 (s, 1H), 12.0 (s, 1H)

Compound XI: Anal. Calcd for $C_{15}H_{20}NO_3Cl$: C, 60.48, H, 6.78, N, 4.70 Found: C, 60.4, H, 6.68, N, 4.53. $^1$H NMR (300 MHz, DMSO-$d_6$): δ 1.28 (m, 6H) 1.48 (m, 4H) 2.19 (t, 2H) 3.19 (qt, 2H), 7.323–7.48 (m, 4H), 8.39 (t, 1H), 12.09 (s, 1H)

Compound XII: Anal. Calcd for $C_{17}H_{22}NO_3$: C, 66.42, H, 7.23, N, 4.56 Found: C, 65.80, H, 7.17, N, 4.14. $^1$H NMR (300 MHz, DMSO-$d_6$): δ 1.25 (m, 6H) 1.43–1.49 (m, 4H) 2.18 (t, 2H) 3.15 (qt, 2H), 6.72 (d, 1H), 7.21–7.26 (m, 2H), 7.39 (t, 1H), 7.48 (d, 1H), 7.65 (t, 1H), 8.21 (t, 1H)

Compound XIII: Anal. Calcd for $C_{15}H_{19}NO_3$: C, 60.18, H, 6.41, N, 4.67 Found: C, 60.26, H, 6.53, N, 4.61. $^1$H NMR (300 MHz, DMSO-$d_6$): δ 1.28 (m, 6H), 1.45–1.52 (m, 4H), 2.19 (t, 2H), 2.22 (qt, 2H), 7.13 (m, 2H), 7.43–7.53 (m, 1H), 8.67 (t, 1H) 12.03 (s, 1H)

Compound XIV: Anal. Calcd for $C_{14}H_{20}N_2O_3$: .0.66 $H_2O$: C, 63.04, H, 7.91, N, 10.34 Found: C, 63.21, 7.59, 10.53 $^1$H NMR (300 MHz, DMSO-$d_6$): δ 1.22–12.8 (m, 6H), 1.48–1.50 (m, 4H), 2.18 (t, 2H), 3.24 (qt, 2H), 7.48 (m, 1H), 8.15 (d, 1H), 8.63–8.69 (m, 2H), 8.97 (d, 1H)

Compound XX: Anal. Calcd for $C_{15}H_{20}NO_3F$: C, 60.09, H, 7.19, N, 4.98 Found: C, 63.82, H, 7.23, N, 4.94. $^1$H NMR (300 MHz, DMSO-$d_6$): δ 1.28 (m, 6H) 1.49 (m, 4H) 2.19 (t, 2H) 3.23 (qt, 2H), 7.24–7.30 (m, 2H), 7.49–7.60 (m, 2H), 11.99 (s, 1H)

Compound XXI: Anal. Calcd for $C_{17}H_{23}NO_4$: C, 66.85, H, 7.61, N, 4.58 Found: C, 66.81, H, 7.69, N, 4.37. $^1$H NMR (300 MHz, DMSO-$d_6$): δ 1.26 (m, 6H) 1.42–1.50 (m, 4) 2.18 (t, 2H) 3.13 (qt, 2H), 6.63 (d, 1H), 6.80 (t, 1H), 6.86 (d, 1H), 7.15 (t, 1H), 7.39 (d, 1H), 7.60 (d, 1H), 8.03 (t, 1H), 9,95 (s, 1H), 12.12 (s, 1H)

Compound XXIII: Anal. Calcd for $C_{15}H_{27}NO_3$: C, 66.86, H, 10.22, N, 5.19 Found: C, 66.92, H, 10.72, N, 5.14. $^1$H NMR (300 MHz, DMSO-$d_6$): δ 1.56–1.34 (m, 13H) 1.46 (t, 2H) 1.60–1.68 (m, 5H), 2.04 (t, 1H), 2.17 (t, 2H), 2.97 (qt, 2H), 7.62 (t, 1H), 11.98 (s, 1H)

Compound XXVII: Anal. Calcd for $C_{18}H_{27}NO_4$: C, 67.25, H, 8.48, N, 4.36 Found: C, 67.23, H, 8.57, N, 4.20. $^1$H NMR (300 MHz, DMSO-$d_6$): δ 1.22–1.26 (m, 12H) 1.45–1.51 (m, 4H) 2.16 (t, 2H) 3.25 (qt, 2H), 6.85 (t, 2H), 7.37 (t, 1H), 7.81 (d, 1H), 8.79 (t, 1H), 11.95 (s, 1H), 12.72 (s, 1H)

Compound XXXIII: $^1$H NMR (300 MHz, DMSO-$d_6$): δ 1.2 (a, 2H), 1.3 (q,2H), 1.3 (q, 2H), 1.5 (q, 2H), 2.2 (t, 2H), 3.0 (q, 2H), 3.5 (s, 2H), 7.3 (m, 5H), 8.0 (s, 1H)

Compound XXXIV: Anal. Calcd for $C_{12}H_{17}NO_4$: C, 62.23, H, 6.83, N, 5.57 Found: C, 61.93, H, 6.80, N, 5.56. $^1$H NMR (300 MHz, DMSO-$d_6$): δ 1.24–1.34 (m, 2H) 1.49–1.57 (m, 4H) 2.19 (t, 2H) 3.26 (qt, 2H), 6.68 (t, 2H), 7.37 (s, 1H), 7.83 (d, 1H) 8.81 (t, 1H), 12.08 (s, 1H), 12.72 (s, 1H)

EXAMPLE 2

Compound XIX was prepared as follows:

A 5 L three-neck round bottom flask was fitted with a heating mantle, an overhead mechanical stirrer, an addition funnel, and a thermometer. The reaction was performed under an argon atmosphere. Hydroxylamine-O-sulfonic acid (196.7 g, 1.74 moles, 1.10 equiv.) and formic acid (1 L) were charged into the round bottom flask and stirred to form a white slurry. A solution of cyclooctanone (200.0 g 1.58 moles, 1.0 equiv.) in formic acid (600 mL) was added dropwise to the white slurry via the addition funnel. After the addition, the addition funnel was replaced by a reflux condenser, and the reaction was heated to reflux (internal temperature about 105° C.) for 1 hour to give a brown solution. After the solution was cooled to room temperature, it was poured into a mixture of saturated aqueous ammonium chloride (1.5 L) and water (1.5 L). The aqueous mixture was extracted with chloroform (3×1200 mL). The combined chloroform layers were transferred into a beaker, and saturated sodium bicarbonate (2 L) was added slowly. The chloroform layer was then separated, dried over anhydrous sodium sulfate, and evaporated under reduced pressure to afford a brown oil. The oil was placed in a 500 mL round bottom flask with a magnetic stirrer. The round bottom flask was placed in a silicon oil bath and was fitted with a short path vacuum distillation head equipped with a thermometer. A Cow-type receiver was connected to three 250 mL flasks. 2-Azacyclononanone (145 g, 65%, mp 64–69° C.) was obtained by vacuum distillation (fraction with head temperature range from 80 to 120° C. at pressures between 3.0 and 3.4 mmHg).

A 5 L three-neck round bottom flask was fitted with a heating mantle, an overhead mechanical stirrer, a reflux condenser, and a thermometer. A suspension of 2-azacyclononanone (83 g, 0.59 moles, 1.0 equiv.) in 5M aqueous sodium hydroxide (650 mL, 3.23 moles, 5.5 equiv.) was charged into the round bottom flask. The mixture was heated to reflux (internal temperature about 110° C.) for 4 hours to yield a clear yellow solution. The heating mantle and reflux condenser were removed. After the solution cooled to room temperature, it was diluted with water (650 mL) and cooled further in an ice bath. Finely ground O-acetylsalicyloyl chloride (114.7 g, 0.59 moles, 1.0 equiv.) was added portionwise to the solution with stirring and continued cooling over 1 hour. After an additional 30 minutes, the ice-bath was removed and stirring was continued at ambient temperature for 21 hours to give a brownish yellow solution. The stirred mixture was acidified with 2M sulfuric acid (about 850 mL) to a pH of about 1, and a yellow solid was formed. The solid was collected by filtration and was dissolved in warm methanol (1.7 L). Activated charcoal (about 5 g) was added to the methanol, and the solution was stirred for 1 0 minutes. The activated charcoal was removed by filtration, and the charcoal residue was washed with additional 300 mL methanol. Water (2 L) was added to the combined filtrates (i.e. the 2 L methanol), and an off-white solid precipitated upon standing at 4° C. overnight. The crude product was filtered and was recrystallized from 65% methanol/water (v/v) to yield Compound XVIII (69.1 g, 42%) as off-white solid.

Properties are listed below:

mp 116–117° C.; HPLC, $^1$H NMR and Anal. Calcd for $C_{15}H_{21}NO_4$: C, 64.50; H, 7.58; N, 5.02. Found: C, 64.26; H, 7.81; N, 4.93.

EXAMPLES 3–13

In Vivo Evaluation of Recombinant Growth Hormone in Rats

Dosing compositions were prepared by mixing the modified amino acids and recombinant human growth hormone (rhGH) as listed in Table 1 below in a phosphate buffer solution at a pH of about 7–8.

Rats were administered the dosing composition by sublingual, oral gavage, intraduodenal administration, or colonic administration. Delivery was evaluated by using an ELISA assay for rhGH, from Medix Biotech, Inc. For intracolonic administration, a sample was prepared and dosed to fasted rats at 25 mg/kg of carrier in a buffered solution containing propylene glycol (0–50%) and 1 mg/kg rhGH.

Results are illustrated in Table 1 below.

Comparative Example 3A rhGH (6 ml/mg) was administered by oral gavage to a rat, and delivery was evaluated according to the procedure of Example 3.

Results are illustrated in Table 1 below.

TABLE 1

In Vivo Delivery of rhGH

| Example | Carrier | Carrier Dose (ng/mL) | Drug Dose (mg/mL) | Method of Administration | Mean Peak Serum Levels of rhGH (ng/mL) |
|---|---|---|---|---|---|
| 3 | I | 500 | 6 | oral | 26.6 +/− 43.83 |
| 3A | none | 0 | 6 | oral | <10 +/− 10 |
| 4 | V | 500 | 6 | oral | 3.22 +/− 7.2 |
| 5 | VI | 500 | 6 | oral | 19.34 +/− 18.73 |
| 6 | VIII | 500 | 6 | oral | 73.41 +/− 70.3 |
| 7 | IX | 500 | 6 | oral | 28.70 +/− 41.7 |
| 8 | XIII | 25 | 1 | colonic | 109.52 +/− 36.1 |
| 9 | XIX | 200 | 3 | oral | 60.92 +/− 26.3 |
| 10 | XIX | 25 | 1 | colonic | 111.52 +/− 16.4 |
| 11 | XIX | 100 | 3 | sublingual | 119.14 +/− 65.6 |
| 12 | XIX | 25 | 1 | intranasal | 92.7 +/− 73.2 |
| 13 | XXVII | 25 | 1 | colonic | 73.72 +/− 4.9 |

EXAMPLES 14–19

In Vivo Evaluation of Interferon in Rats

Dosing compositions were prepared by mixing the modified amino acid compounds and interferon α2b as listed in Table 2 below in a "TRIZMA®" base(tris(hydroxymethyl) aminomethane buffer solution (Tris-HCl) at a pH of about 7–8. Propylene glycol (0–25%) was added as a solubilizing agent, if necessary.

Rats were administered the dosing composition by oral gavage, intraduodenal administration, or intracolonic administration. Delivery was evaluated by use of an ELISA assay for human interferon a from Biosource, Inc.

Results of intracolonic administration are illustrated in Table 2 below.

Comparative Example 14A

Interferon α2b (25 mg/mL) was administered intracolonically to rats, and delivery was evaluated according to the procedure of Example 14.

Results are illustrated in Table 2 below.

TABLE 2

In Vivo Delivery of Interferon by Intracolonic Administration

| Example | Carrier | Carrier Dose (ng/mL) | Interferon Dose (mg/kg) | Mean Peak Serum Levels of Interferon (pg/mL) |
|---|---|---|---|---|
| 14 | VII | 100 | 25 | 5241 +/− 2205 |
| 14A | none | 0 | 25 | 0 |
| 15 | XI | 100 | 25 | 1189 +/− 1373 |
| 16 | XII | 100 | 25 | 6955 +/− 2163 |
| 17 | XIX | 100 | 25 | 11193 +/− 8559 |
| 18 | XXI | 100 | 25 | 4238 +/− 2789 |
| 19 | XXXIV | 100 | 25 | 4853 +/− 5231 |

EXAMPLES 20–23

In Vivo Evaluation of Salmon Calcitonin in Rats

Dosing compositions were prepared by mixing the modified amino acids and salmon calcitonin as listed in Table 3 below. 400 mg of carrier were added to 2.9 mL of 25% aqueous propylene glycol. The resultant solution was stirred, and the pH was adjusted to 7.2 with sodium hydroxide (1.0N). Water was added to bring the total volume to 2.0 mL. The sample had a final carrier concentration of 200 mg/mL. Calcitonin (10 μg) was added to the solution. The total calcitonin concentration was 2.5 μg/mL.

For each sample a group of fasted rats were anesthetized. The rats were administered the dosing composition by oral gavage, intracolonic instillation, or intraduodenal administration. Blood samples were collected serially from the tail artery. Serum calcium was determined by testing with a Calcium Kit (Sigma Chemical Company, St. Louis, Mo., USA).

Results are illustrated in Table 3 below.

TABLE 3

In Vivo Delivery of Calcitonin

| Example | Carrier | Carrier Dose (ng/mL) | Drug Dose (mg/mL) | Method of Administration | Maximum Decrease in Serum Calcium (% below baseline) |
|---|---|---|---|---|---|
| 20 | I | 400 | 10 | oral | |
| 21 | V | 400 | 10 | oral | 18.35 +/− 2.87 |
| 22 | XIX | 10 | 3 | intracolonic | 26.49 +/− 12.3 |
| 23 | XIX | 200 | 7.5 | oral | 25.48 +/− 4.7 |

EXAMPLES 24–28

In Vivo Evaluation of Heparin in Rats

Dosing compositions were prepared by mixing the modified amino acids and heparin as listed in Table 4. In a test tube, 900 mg of carrier were dissolved in 3 mL of propylene glycol, and 0.299 g of sodium heparin was dissolved in 3 mL of water. The solutions were mixed by vortex. Sodium hydroxide (10M) was added to the resulting mixture until a solution was obtained. The pH was then adjusted to 7.4±0.5 with concentrated hydrochloric acid, and the final solution was sonicated at 40° C. for 30 minutes.

A group of fasted, conscious rats were administered the dosing compositions by oral gavage. Blood samples were collected by cardiac puncture following the administration of ketamine (44 mg/kg)., Heparin activity was determined by utilizing the activated partial thromboblastim time (APTT) according to the method of Henry, J. B., *Clinical Diagnosis and Management by Laboratory Methods;* Philadelphia, Pa.; W. B. Saunders (1979).

Results are illustrated in Table 4 below.

Comparative Example 24A

Heparin (100 mg/mL) was administered by oral gavage to rats, and heparin activity was determined according to the procedure of Example 24.

Results are illustrated in Table 4 below.

TABLE 4

In Vivo Delivery of Heparin by Oral Administration

| Example | Carrier | Carrier Dose (mg/kg) | Drug Dose (mg/mL) | Mean Peak APTT (sec) |
|---|---|---|---|---|
| 24 | II | 300 | 100 | 25.45 +/− 2.8 |
| 24A | none | none | 100 | 20.7 +/− 0.17 |
| 25 | III | 300 | 100 | 38.64 +/− 17 |
| 26 | V | 300 | 100 | 87.4 +/− 34.1 |

TABLE 4-continued

In Vivo Delivery of Heparin by Oral Administration

| Example | Carrier | Carrier Dose (mg/kg) | Drug Dose (mg/mL) | Mean Peak APTT (sec) |
|---|---|---|---|---|
| 27 | XII | 300 | 100 | 49.53 +/− 17.1 |
| 28 | XIX | 300 | 100 | 119.99 +/− 56.3 |

EXAMPLE 29

The method of Example 24 was followed, substituting low molecular weight heparin for the heparin and varying the amounts of propylene glycol and water for solubilization as, necessary.

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A compound selected from the group consisting of

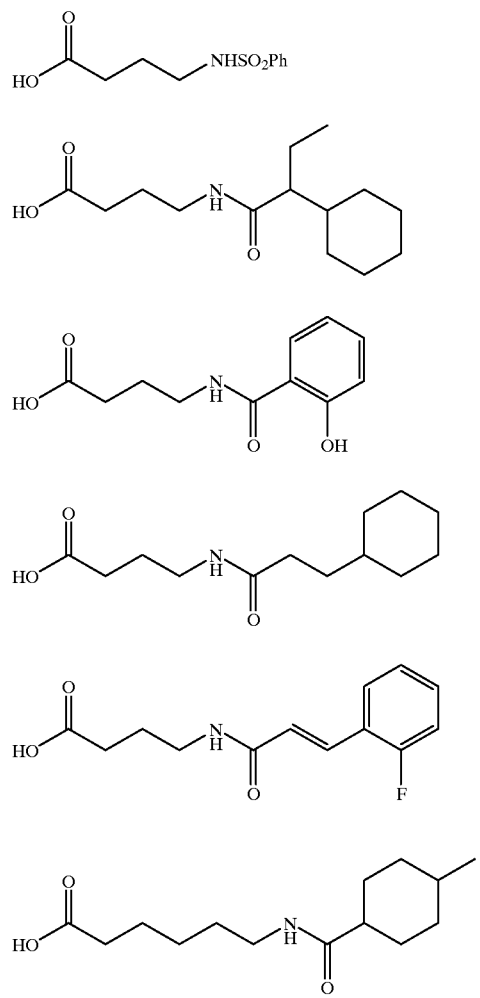
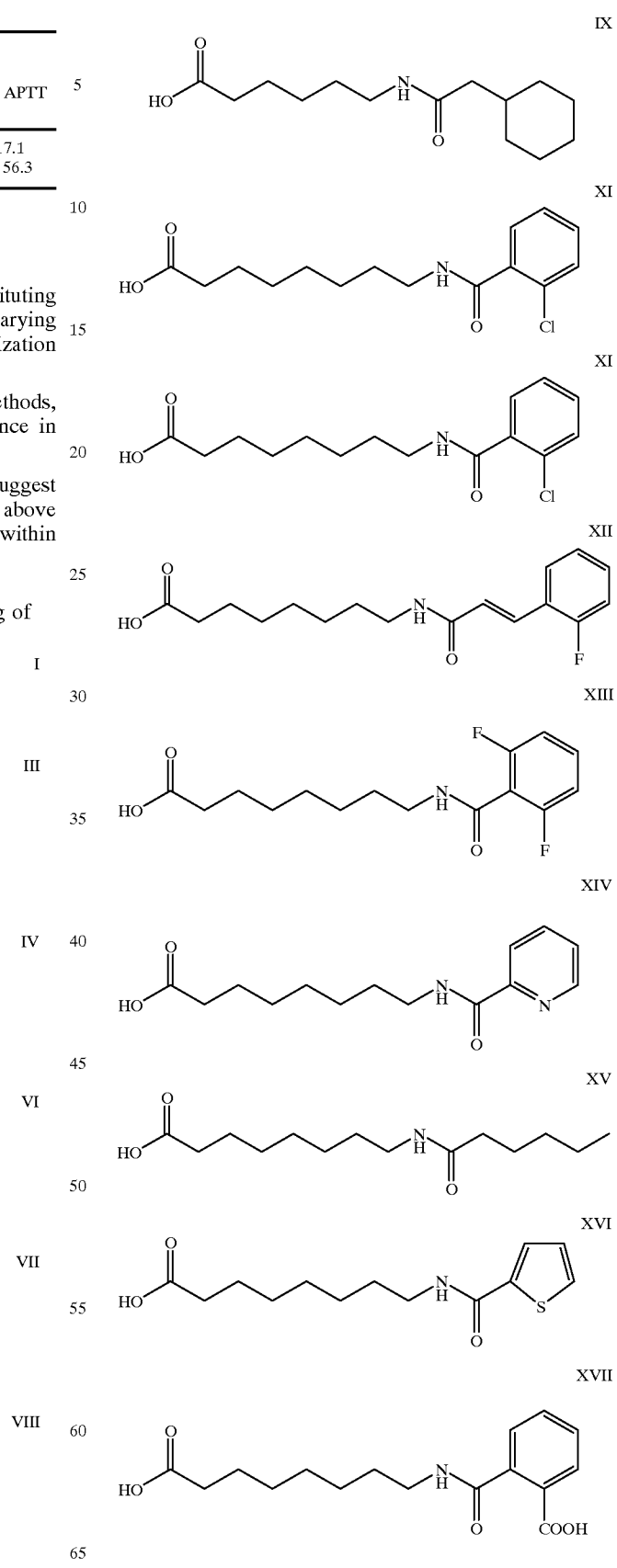

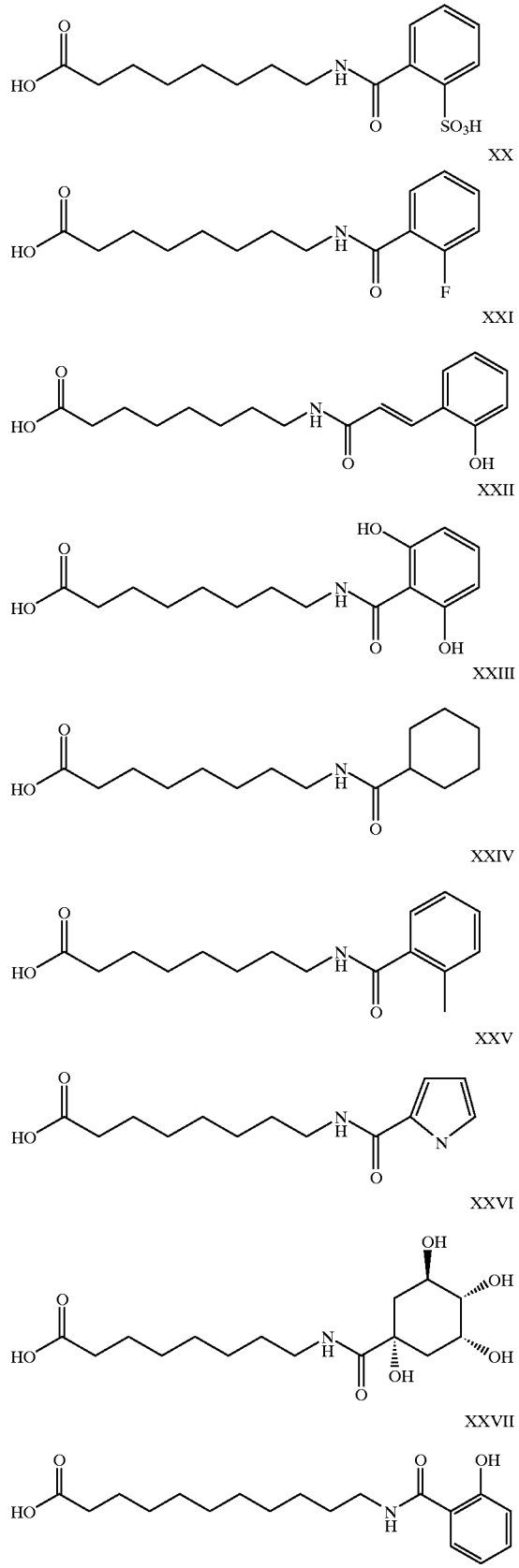
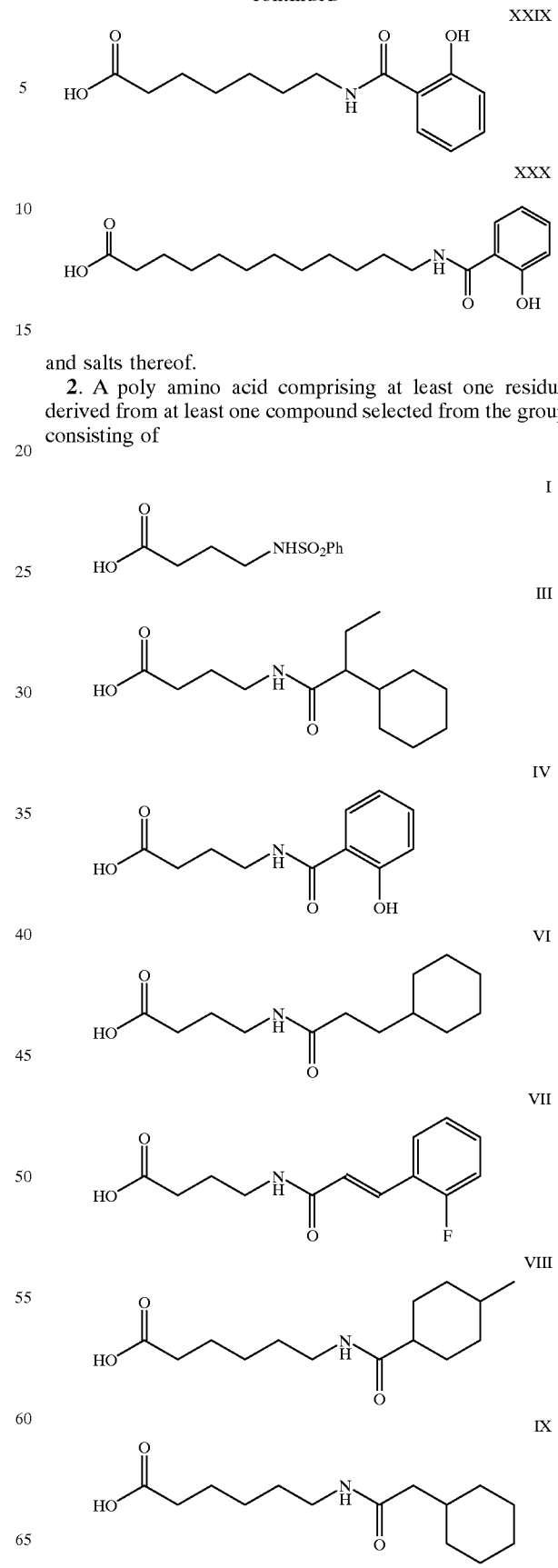
and salts thereof.
2. A poly amino acid comprising at least one residue derived from at least one compound selected from the group consisting of

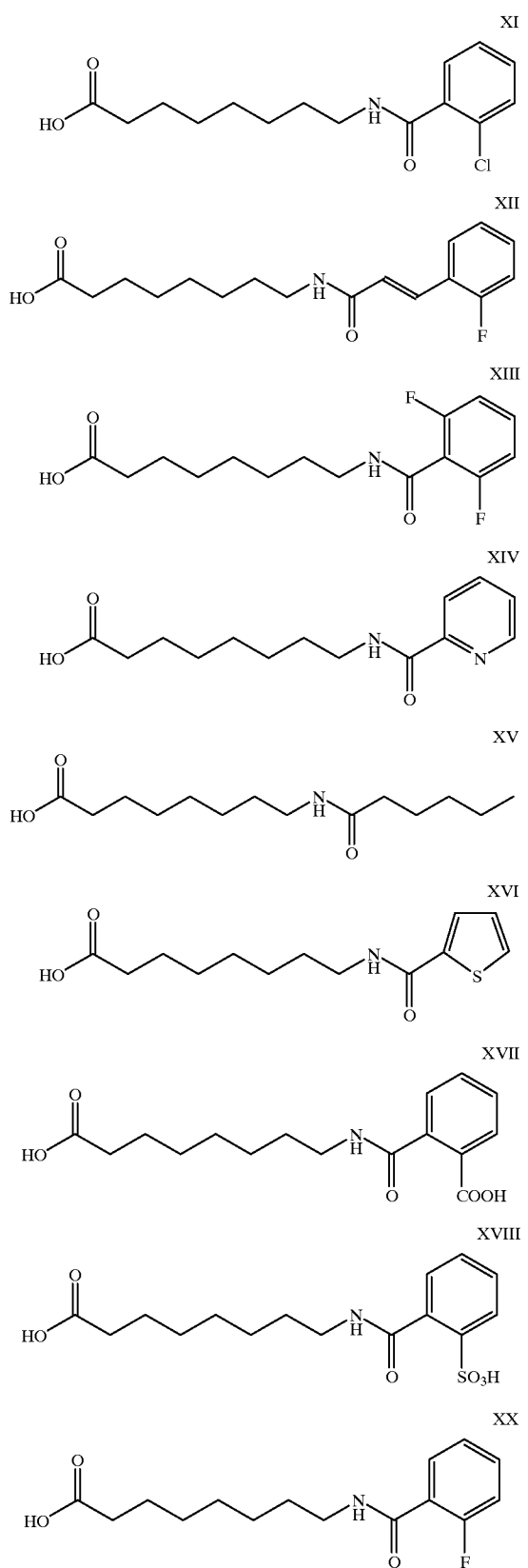
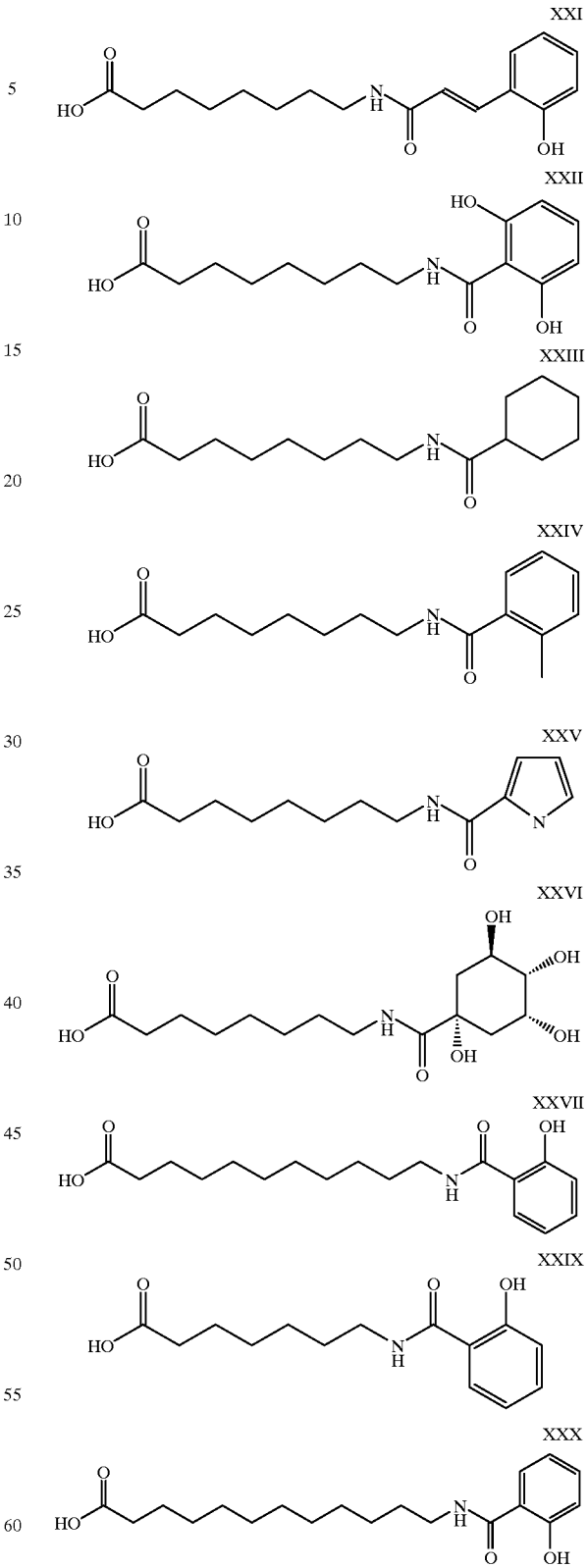
and salts thereof.

3. A poly amino acid as defined in claim 2, comprising a peptide.
4. A composition comprising
(a) an active agent; and
(b) a compound selected from the group consisting of
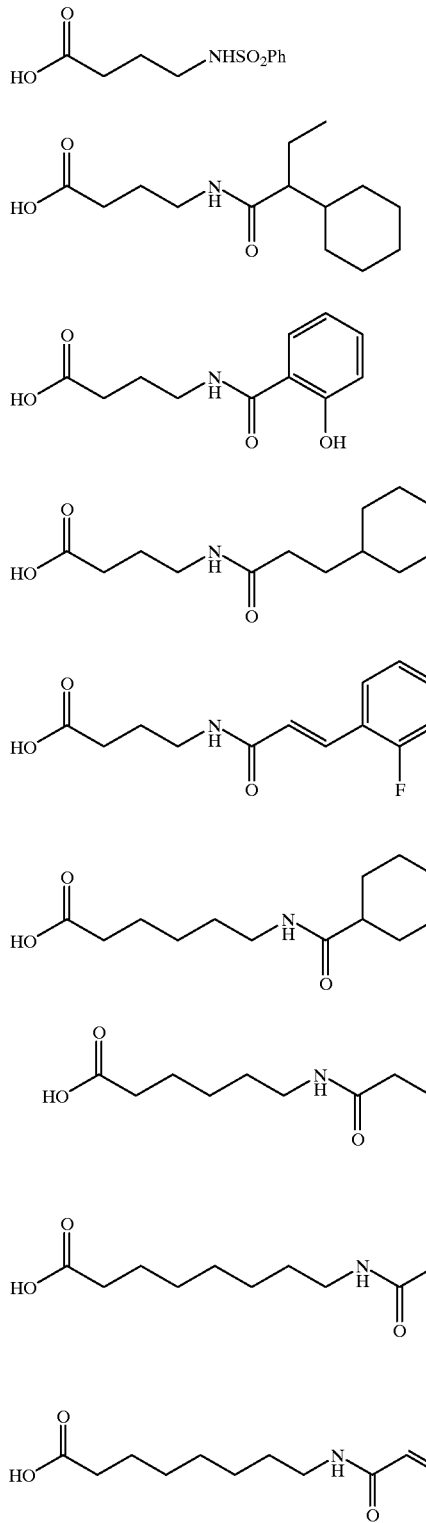
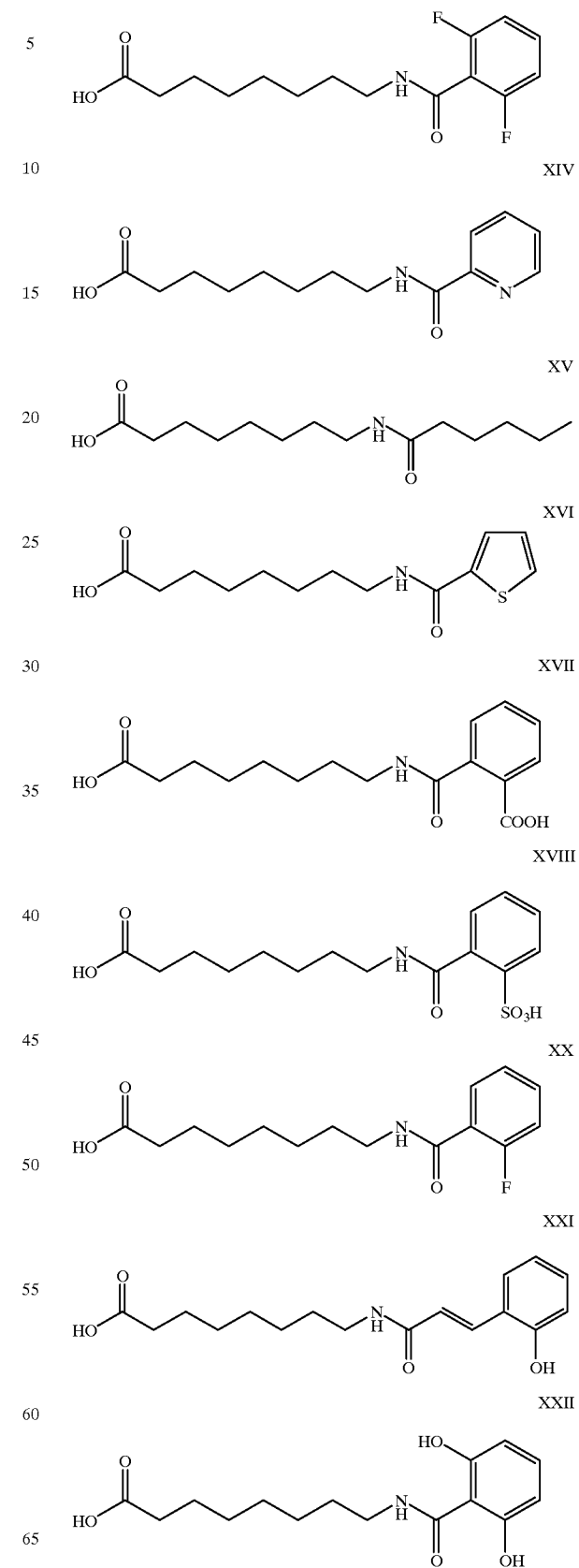

XXIII
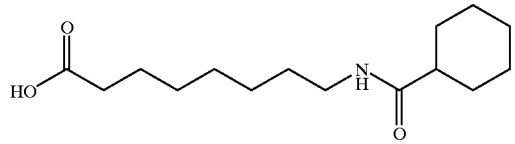
XXIV
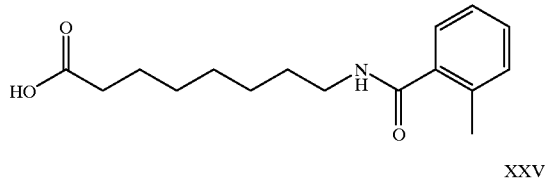
XXV
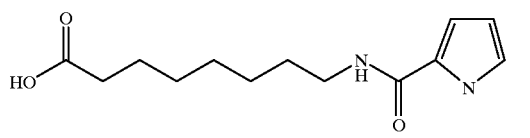
XXVI
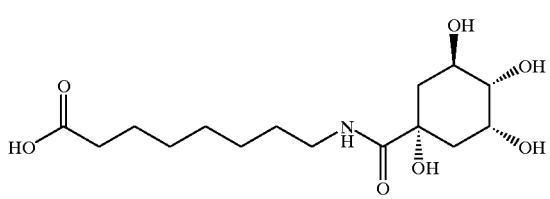
XXVII
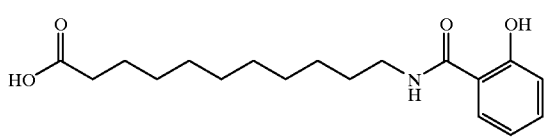
XXIX
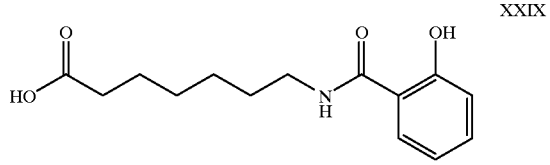
XXX
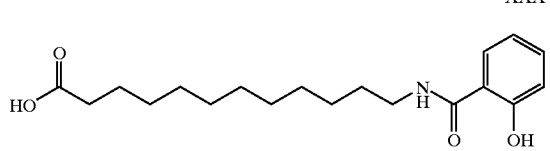
XXXII
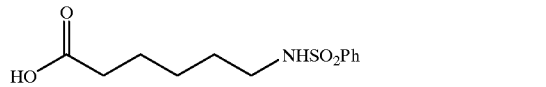
XXXIV
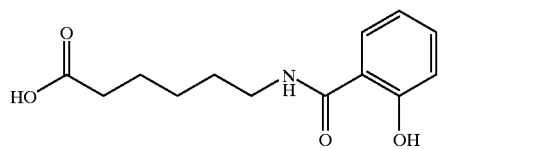
XXXV
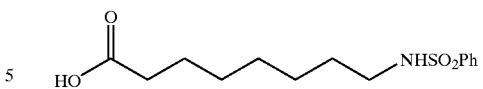
and salts thereof.
5. A composition comprising
(a) an active agent; and
(b) a poly amino acid comprising at least one residue derived from an amino acid selected from the group consisting of
I
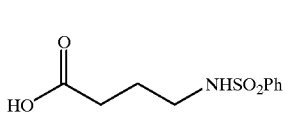
III
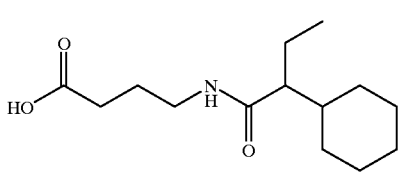
IV
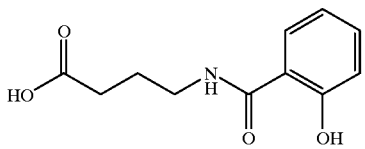
VI
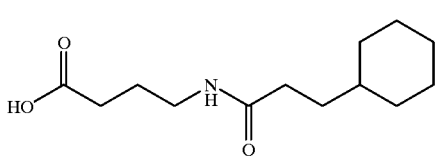
VII
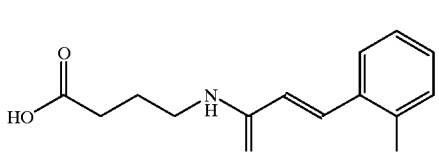
VIII
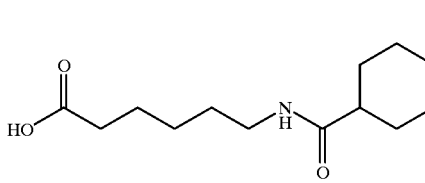
IX
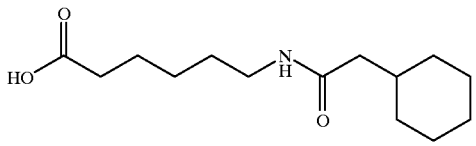

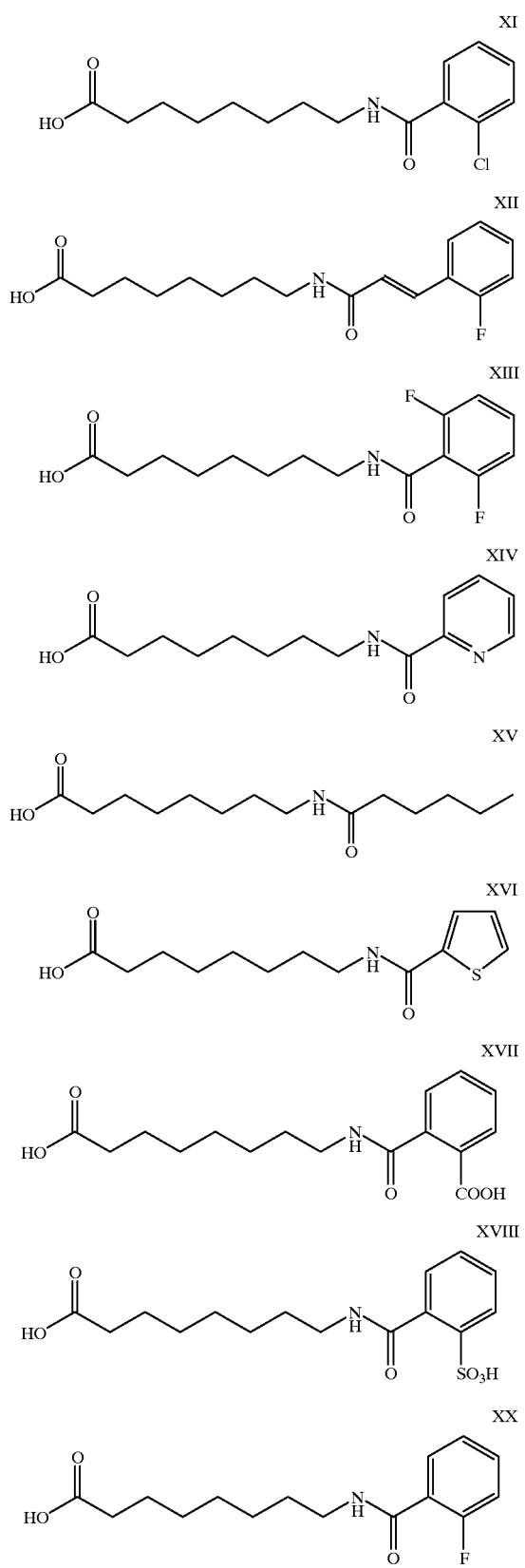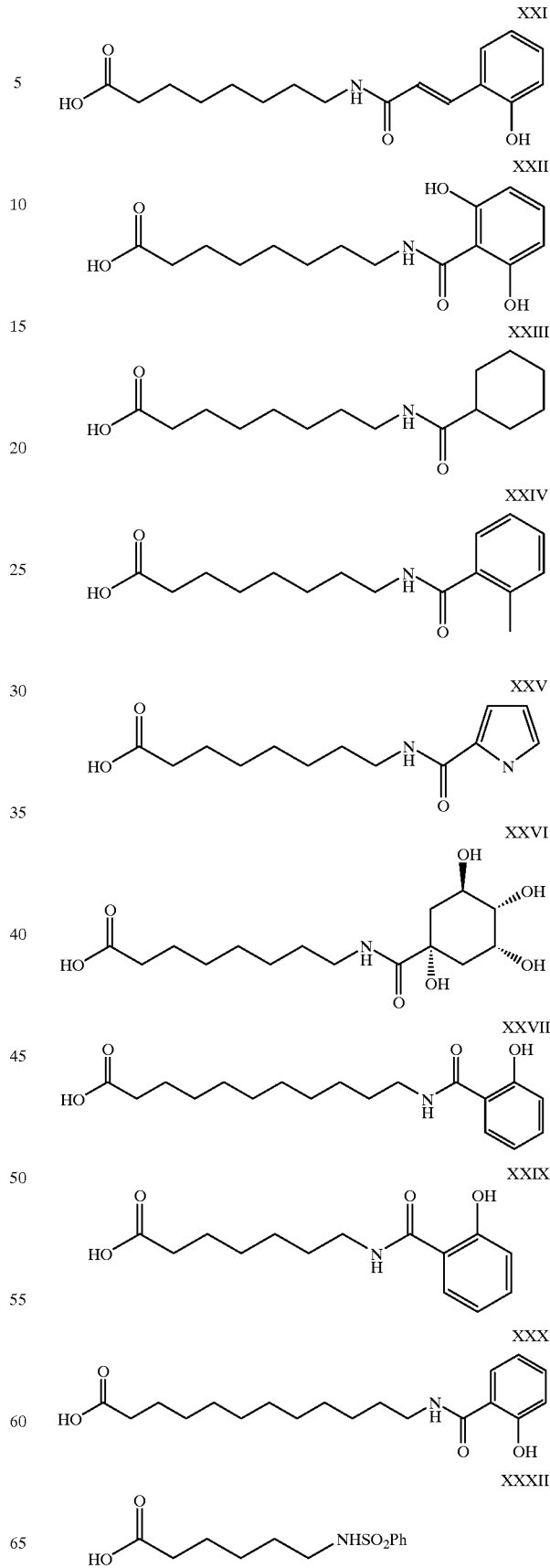

-continued

XXXIV (structure: HO-C(=O)-(CH2)4-NH-C(=O)-C6H4-OH)

XXXV (structure: HO-C(=O)-(CH2)7-NHSO2Ph)

and salts thereof.

6. A composition as defined in claim 5, wherein said poly amino acid comprises a peptide.

7. A composition as defined in claim 4, wherein said active agent is selected from the group consisting of a biologically active agent and a chemically active agent.

8. A composition as defined in claim 7, wherein said biologically active agent is selected from the group consisting of a peptide, a mucopolysaccharide, a carbohydrate, a lipid, a pesticide, and any combination thereof.

9. A composition as defined in claim 8, wherein said biologically active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), and any combination thereof.

10. A composition as defined in claim 5, wherein said active agent is selected from the group consisting of a biologically active agent and a chemically active agent.

11. A composition as defined in claim 10, wherein said biologically active agent is selected from the group consisting of a peptide, a mucopolysaccharide, a carbohydrate, a lipid, a pesticide, and any combination thereof.

12. A composition as defined in claim 11, wherein said biologically active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), and any combination thereof.

13. A composition as defined in claim 6, wherein said active agent is selected from the group consisting of a biologically active agent and a chemically active agent.

14. A composition as defined in claim 13, wherein said biologically-active agent is selected from the group consisting of a peptide, a mucopolysaccharide, a carbohydrate, a lipid, a pesticide, and any combination thereof.

15. A composition as defined in claim 14, wherein said biologically-active agent is selected from the group consisting of human growth hormone, bovine growth hormone, growth hormone-releasing hormone, an interferon, interleukin-II, insulin, heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, desferrioxamine (DFO), and any combination thereof.

16. A dosage unit form comprising
(A) a composition as defined in claim 4; and
(B)
 (a) an excipient,
 (b) a diluent,
 (c) a disintegrant,
 (d) a lubricant,
 (e) a plasticizer,
 (f) a colorant,
 (g) a dosing vehicle, or
 (h) any combination thereof.

17. A dosage unit form according to claim 16, comprising a tablet, a capsule, or a liquid.

18. A dosage unit form comprising
(A) a composition as defined in claim 5; and
(B)
 (a) an excipient,
 (b) a diluent,
 (c) a disintegrant,
 (d) a lubricant,
 (e) a plasticizer,
 (f) a colorant,
 (g) a dosing vehicle, or
 (h) any combination thereof.

19. A dosage unit form according to claim 18, comprising a tablet, a capsule, or a liquid.

20. A dosage unit form comprising
(A) a composition as defined in claim 6; and
(B)
 (a) an excipient,
 (b) a diluent,
 (c) a disintegrant,
 (d) a lubricant,
 (e) a plasticizer,
 (f) a colorant,
 (g) a dosing vehicle, or
 (h) any combination thereof.

21. A dosage unit form according to claim 20, comprising a tablet, a capsule, or a liquid.

22. A method for administering a biologically-active agent to an animal in need of said agent, said method comprising administering orally to said animal a composition as defined in claim 4.

23. A method for administering a biologically-active agent to an animal in need of said agent, said method comprising administering orally to said animal a composition as defined in claim 5.

24. A method for administering a biologically-active agent to an animal in need of said agent, said method comprising administering orally to said animal a composition as defined in claim 6.

25. A method for preparing a composition, said method comprising mixing:
(A) at least one biologically-active agent;
(B) at least one compound as defined in claim 1; and
(C) optionally a dosing vehicle.

26. A method for preparing a composition, said method comprising mixing:
(A) at least one biologically-active agent;
(B) at least one poly amino acid as defined in claim 2; and
(C) optionally a dosing vehicle.

27. A method for preparing a composition, said method comprising mixing:
(A) at least one biologically-active agent;
(B) at least one peptide as defined in claim 3; and
(C) optionally a dosing vehicle.

28. A method for preparing a compound having the formula

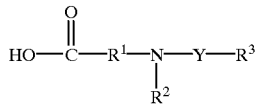

XXXVI wherein Y is

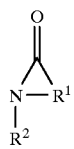

Y is C or SO$_2$;

$R^1$ is $C_3$–$C_{24}$ alkyl, $C_2$–$C_{20}$ alkenyl, $C_2$–$C_{20}$ alkyne, cycloalkyl, or aromatic;
$R^2$ is hydrogen, $C_1$–$C_4$ alkyl, or $C_2$–$C_4$ alkenyl; and
$R^3$ is $C_1$–$C_7$ alkyl, $C_3$–$C_{10}$ cycloalkyl, aryl, thienyl, pyrrolo, or pyridyl, where $R^3$ is optionally substituted by one or more $C_1$–$C_5$ alkyl group, $C_2$–$C_4$ alkenyl group, F, Cl, OH, SO$_2$, COOH and SO$_3$H; said method comprising
(a) reacting in water and the presence of a base, a compound having the formula

XXXVIII

with a compound having the formula

R$^3$—Y—X, wherein Y, $R^1$, $R^2$, and $R^3$ are as above and X is a leaving group.

29. A composition for oral delivery of a biologically active agent, said composition comprising (a) a biologically active agent; and
(b) an oral delivery effective amount of at least one compound selected from the group consisting of

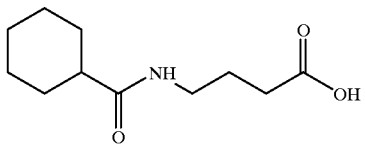

V

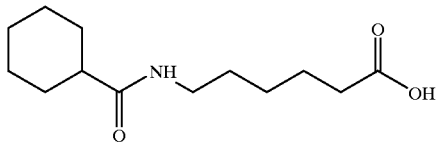

XXXI

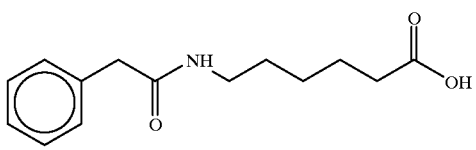

XXXIII a poly amino acid derived from at least one compound selected from the group consisting of compounds V, XXXI, and XXXIII, and salts thereof, wherein said biologically active agent comprises at least one peptide, mucopolysaccharide, carbohydrate, or lipid.

30. A composition as defined in claim 29, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, somatostatin, adrenocorticotropin, gonadotropin releasing hormone, oxytocin, vasopressin, cromolyn sodium, vancomycin, parathyroid hormone, desferrioxamine (DFO), and any combination thereof.

* * * * *

UNITED STATES PATENT AND TRADEMARK OFFICE
CERTIFICATE OF CORRECTION

PATENT NO.    :   6,071,510
DATED         :   June 6, 2000
INVENTOR(S)   :   Andrea Leone-Bay et al.

It is certified that errors appear in the above-identified patent and that said Letters Patent is hereby corrected as shown below:

Title page, [75] Inventors: Please change "Mt. Kisco, N.Y." to -- Monmouth Junction, N.J. -- and "Long Island, N.Y." to -- Long Island City, N,Y. --.

Signed and Sealed this

Twenty-seventh Day of March, 2001

Attest:

NICHOLAS P. GODICI

Attesting Officer

*Acting Director of the United States Patent and Trademark Office*